United States Patent
Ben Yehuda et al.

(10) Patent No.: US 11,273,201 B2
(45) Date of Patent: Mar. 15, 2022

(54) COMPOSITIONS AND METHODS FOR INDUCING THROMBOPOIESIS

(71) Applicant: Hadasit Medical Research Services and Development Ltd., Jerusalem (IL)

(72) Inventors: Dina Ben Yehuda, Mevaseret Zion (IL); Ihab Abd-Elrahman, Abu Gosh (IL); Riki Perlman, Beit-Zayit (IL); Marjorie Pick, Jerusalem (IL)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 128 days.

(21) Appl. No.: 16/392,685

(22) Filed: Apr. 24, 2019

(65) Prior Publication Data

US 2019/0247464 A1    Aug. 15, 2019

Related U.S. Application Data

(62) Division of application No. 14/534,394, filed on Nov. 6, 2014, now Pat. No. 10,307,462.

(60) Provisional application No. 61/900,417, filed on Nov. 6, 2013.

(51) Int. Cl.
| | |
|---|---|
| *C12N 15/85* | (2006.01) |
| *A61K 38/17* | (2006.01) |
| *C12N 5/078* | (2010.01) |
| *C12N 5/0789* | (2010.01) |
| *A61K 45/06* | (2006.01) |
| *A61K 35/28* | (2015.01) |
| *A61K 35/545* | (2015.01) |

(52) U.S. Cl.
CPC .......... *A61K 38/1761* (2013.01); *A61K 35/28* (2013.01); *A61K 35/545* (2013.01); *A61K 45/06* (2013.01); *C12N 5/0644* (2013.01); *C12N 5/0647* (2013.01); *C12N 2501/48* (2013.01); *C12N 2501/727* (2013.01); *C12N 2501/999* (2013.01)

(58) Field of Classification Search
None
See application file for complete search history.

(56) References Cited

U.S. PATENT DOCUMENTS 7,517,949 B2    4/2009    Ben-Yehuda et al.
2015/0125430 A1    5/2015    Ben Yehuda et al.

OTHER PUBLICATIONS

Official Action dated Feb. 6, 2018 From the US Patent and Trademark Office Re. U.S. Appl. No. 14/534,394. (15 pages).
Official Action dated Jun. 9, 2017 From the US Patent and Trademark Office Re. U.S. Appl. No. 14/534,394. (18 pages).
Official Action dated May 23, 2018 From the US Patent and Trademark Office Re. U.S. Appl. No. 14/534,394. (13 pages).
Restriction Official Action dated Mar. 23, 2017 From the US Patent and Trademark Office Re. U.S. Appl. No. 14/534,394. (9 Paages).
Abd-Elrahman et al. "Livin Expression in Normal Hematopoietic Cells and in Hematologic Malignancies", ASH Annual Meeting Abstracts, Blood, 108: # 4301, 2006.
Abd-Elrahman et al. "The Inhibitor of Apoptosis Protein Livin (ML-IAP) Plays A Dual Role in Tumorigenicity", Cancer Research, 69(13): 5475-5480, Jul. 1, 2009.
Abd-Elrahman et al. "The Role of Livin, An Inhibitor of Apoptosis Protein, in Thrombopoiesis", ASH Annual Meeting, Poster Session, Blood, 112: # 1842, 2008.
Abd-Elrahman et al. "The Role of the IAP Livin in Megakaryocytes Differentiation and Thromboiesis", ASH Annual Meeting, Poster Sessions, Blood, 120: # 3297, 2012.
Ashhab et al. "Two Splicing Variants of A New Inhibitor of Apoptosis Gene With Different Biological Properties and Tissue Distribution Pattern", FEBS Letters, 495:56-60, 2001.
Boatright et al. "Mechanisms of Caspase Activation", Current Opinion in Cell Biology, 15(6): 725-731, Dec. 1, 2003.
Chai et al. "Structural Basis of Caspase-7 Inhibition by XIAP", Cell, 104: 769-780, Mar. 9, 2001.
Everett et al. "Point Mutations in the Herpes Simplex Virus Type 1 Vmw110 RING Finger Helix Affect Activation of Gene Expression, Viral Growth, and Interaction with PML-Containing Nuclear Structures", Journal of virology, 69(11): 7339-7344, Nov. 1995.
Huang et al. "Structural Basis of Caspase Inhibition by XIAP: Differential Roles of the Linker Versus the BIR Domain", Cell, 104: 781-790, Mar. 9, 2001.
Kasof et al. "Livin, A Novel Inhibitor of Apoptosis Protein Family Member", The Journal of Biological Chemistry, 276(5): 3238-3246, Feb. 2, 2001.
Nachmias et al. "Caspase-Mediated Cleavage Converts Livin From An Antiapoptotic to A Proapoptotic Factor: Implications for Drug-Resistant Melanoma", Cancer Research, 63: 6340-6349, Oct. 1, 2003.
Vucic et al. "ML-IAP, A Novel inhibitor of Apoptosis That is Preferentially Expressed in Human Melanomas", Current Biology, 10: 1359-1366, Oct. 17, 2000.

*Primary Examiner* — Michael Szperka

(57)    ABSTRACT

Methods of inducing thrombopoiesis and/or treating thrombocytopenia in a subject are provided. Accordingly there is provided a method comprising contacting stem cells with a differentiation potential towards platelets or hematopoietic progenitor cells derived therefrom with Livin, thereby inducing thrombopoiesis. Also provided is a method comprising contacting cells with a differentiation potential towards platelets with tLivin, thereby inducing thrombopoiesis. Also provided are compositions and isolated population of cells for inducing thrombopoiesis and/or treating thrombocytopenia in a subject.

6 Claims, 8 Drawing Sheets
(5 of 8 Drawing Sheet(s) Filed in Color)
Specification includes a Sequence Listing.

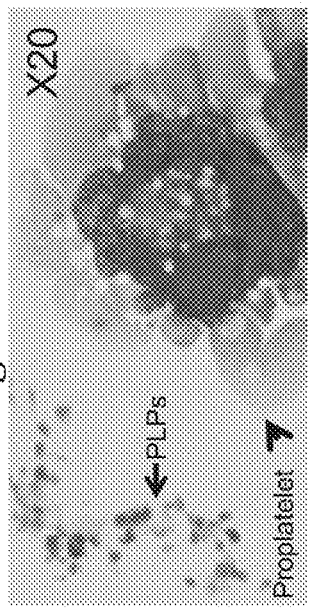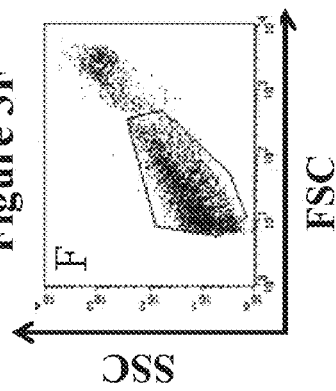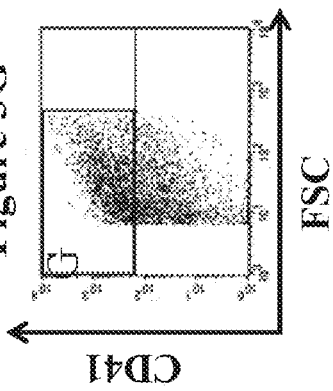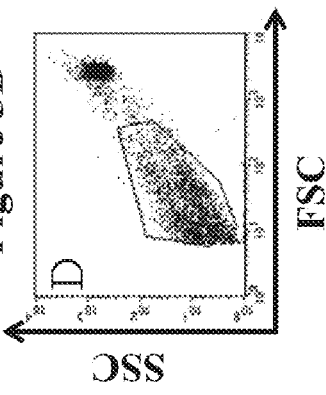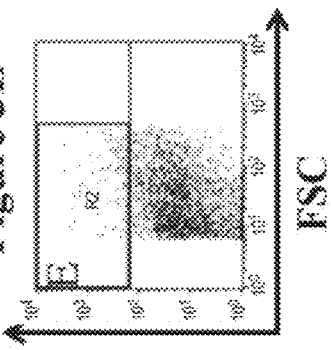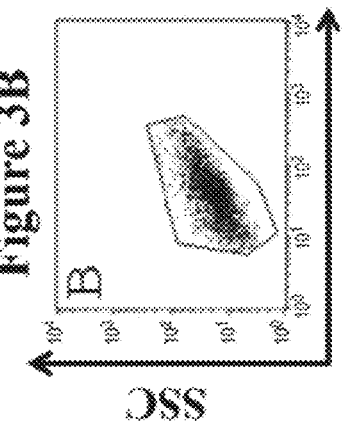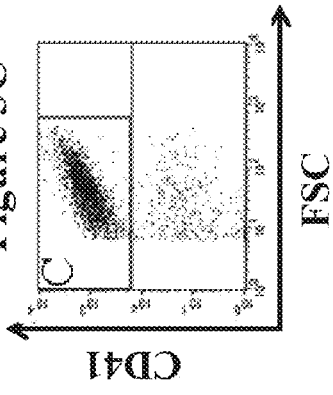

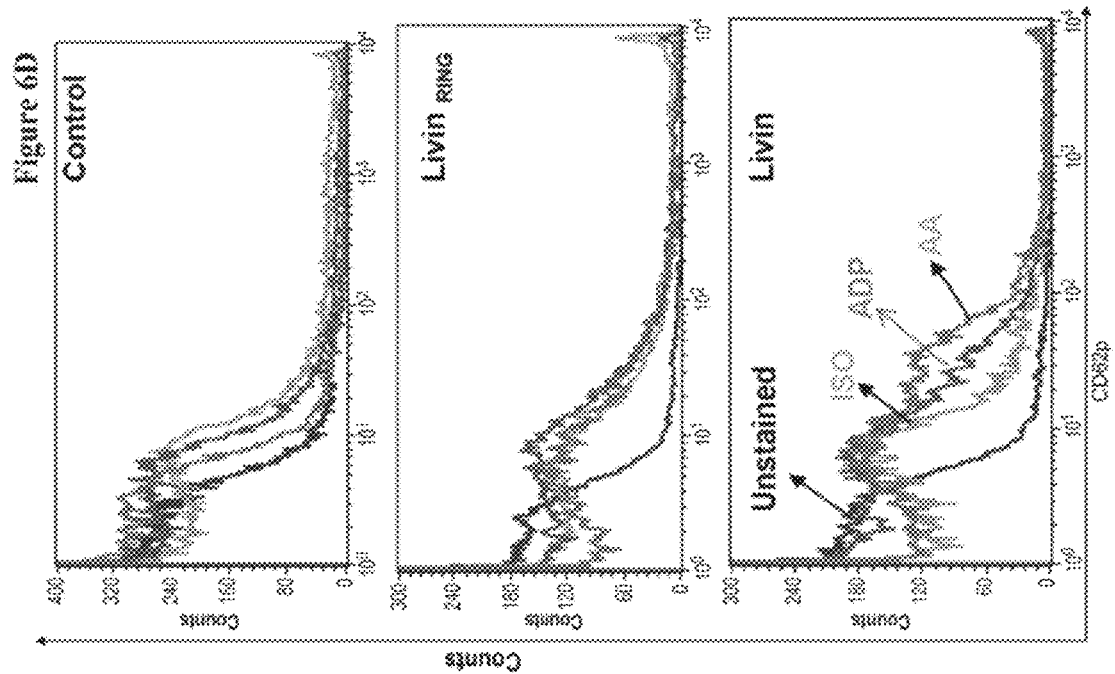
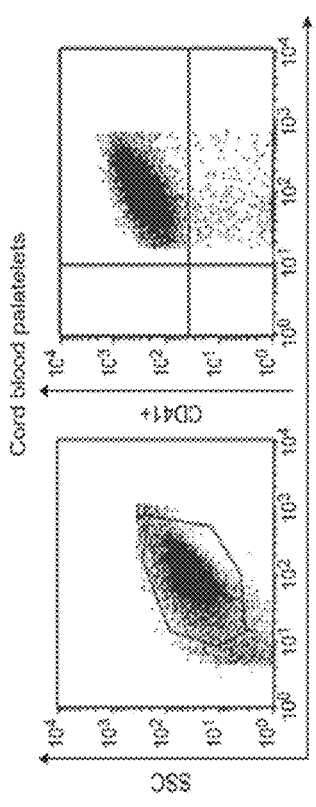
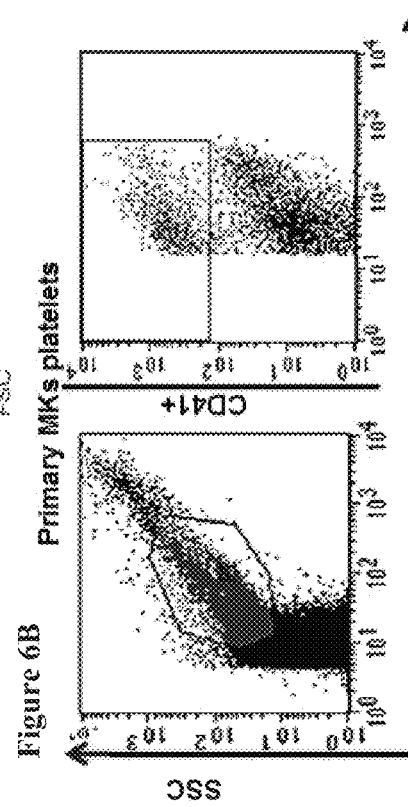
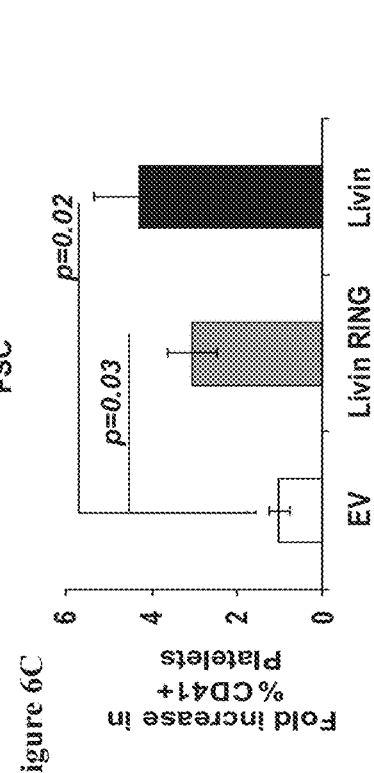

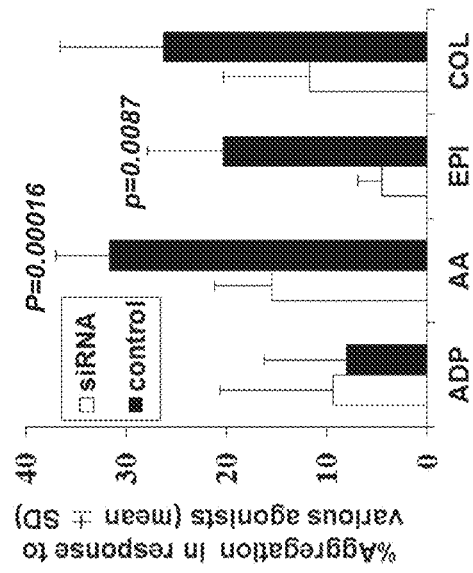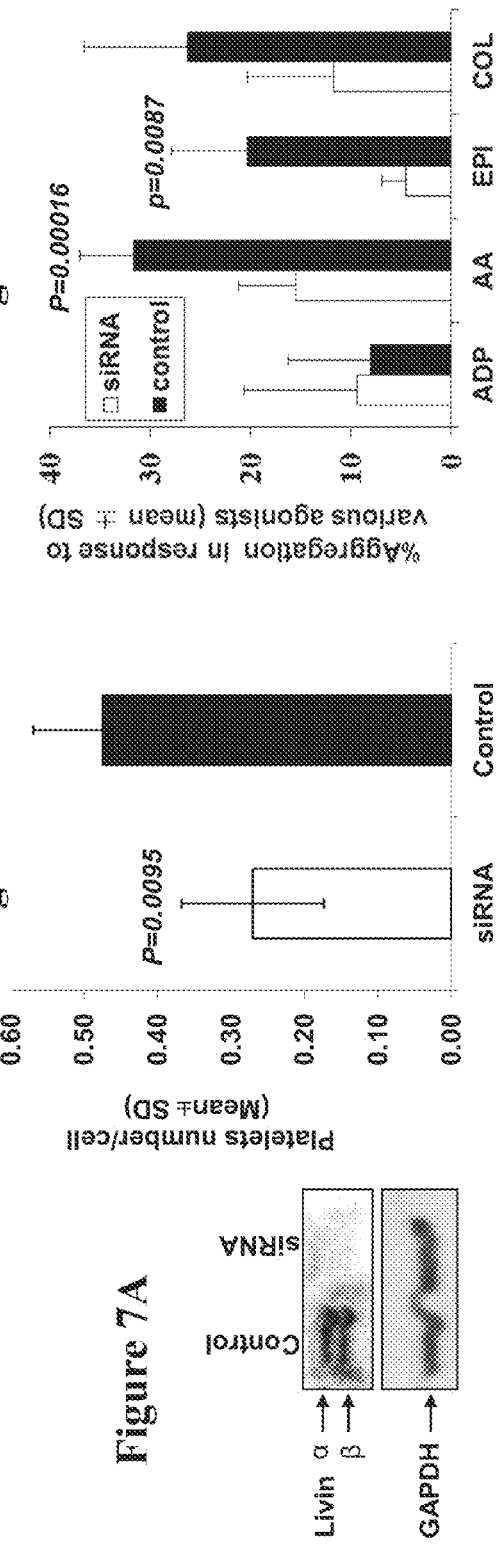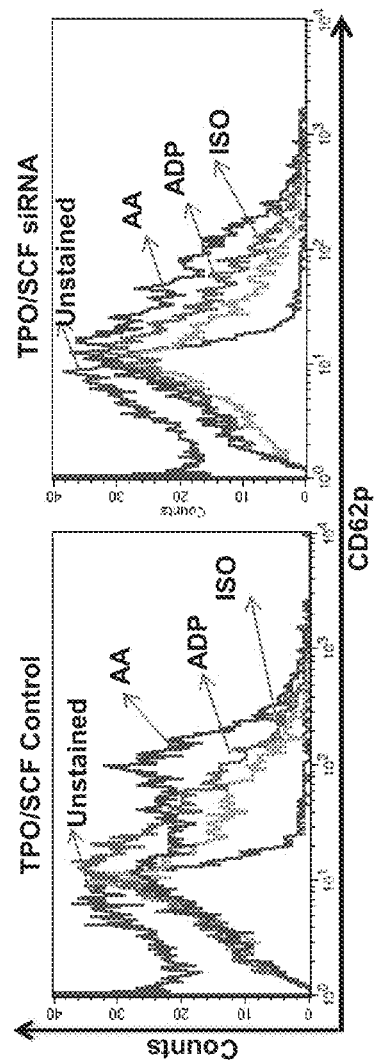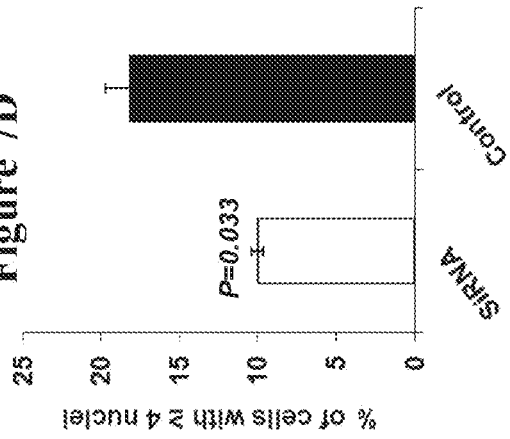

SEQUENCE LISTING

```
<160> NUMBER OF SEQ ID NOS: 13

<210> SEQ ID NO 1
<211> LENGTH: 1387
<212> TYPE: DNA
<213> ORGANISM: Homo sapiens

<400> SEQUENCE: 1
gaccccagag gccaccctgg ccacttccag aaagctgtgg gccctgggat actccctcc        60 cagggtgtct ggtggcaggc ctgtgcctat ccctgctgtc cccagggtgg gccccggggg     120
tcaggagctc cagaagggcc agctgggcat attctgagat tggccatcag cccccatttc     180
tgctgcaaac ctggtcagag ccagtgttcc ctccatggga cctaaagaca gtgccaagtg     240
cctgcaccgt ggaccacagc cgagccactg ggcagccggt gatggtccca cgcaggagcg     300
ctgtggaccc cgctctctgg gcagccctgt cctaggcctg gacacctgca gagcctggga     360
```

```
ccacgtggat gggcagatcc tgggccagct gcggcccctg acagaggagg aagaggagga      420
gggcgccggg gccaccttgt ccagggggcc tgccttcccc ggcatgggct ctgaggagtt      480
gcgtctggcc tccttctatg actggccgct gactgctgag gtgccacccg agctgctggc      540
tgctgccggc ttcttccaca caggccatca ggacaaggtg aggtgcttct ctgctatgg       600 gggcctgcag agctggaagc gcggggacga cccctggacg gagcatgcca agtggttccc      660
cagctgtcag ttcctgctcc ggtcaaaagg aagagacttt gtccacagtg tgcaggagac      720
tcactcccag ctgctgggct cctgggaccc gtgggaagaa ccggaagacg cagcccctgt      780 ggcccccctcc gtccctgcct ctgggtaccc tcgagctgcc cacacccagg agagaggtcc     840
agtctgaaag tgcccaggag ccaggagggg tcagtccagc cgaggcccag agggcgtggt      900
gggttcttga gccccagga gccagggatg tgaggcgca gctgcggcgg ctgcaggagg       960
agaggacgtg caaggtgtgc ctggaccgcg ccgtgtccat cgtctttgtg ccgtgcggcc     1020
acctggtctg tgctgagtgt gccccccggcc tgcagctgtg ccccatctgc agagcccccg   1080
tccgcagccg cgtgcgcacc ttcctgtcct aggccaggtg ccatggccgg ccaggtgggc    1140
tgcagagtgg gctccctgcc cctctctgcc tgttctggac tgtgttctgg gcctgctgag    1200
gatggcagag ctggtgtcca tccagcactg accagccctg attccccgac caccgcccag    1260
ggtggagaag gaggcccttg cttggcgtgg gggatggctt aactgtacct gtttggatgc    1320
ttctgaatag aaataaagtg ggttttccct ggaggtaccc agcagcctga aaaaaaaaaa    1380
aaaaaaa                                                                1387

<210> SEQ ID NO 2
<211> LENGTH: 298
<212> TYPE: PRT
<213> ORGANISM: Homo sapiens

<400> SEQUENCE: 2

Met Gly Pro Lys Asp Ser Ala Lys Cys Leu His Arg Gly Pro Gln Pro
1               5                   10                  15

Ser His Trp Ala Ala Gly Asp Gly Pro Thr Gln Glu Arg Cys Gly Pro
            20                  25                  30

Arg Ser Leu Gly Ser Pro Val Leu Gly Leu Asp Thr Cys Arg Ala Trp
        35                  40                  45

Asp His Val Asp Gly Gln Ile Leu Gly Gln Leu Arg Pro Leu Thr Glu
    50                  55                  60

Glu Glu Glu Glu Glu Gly Ala Gly Ala Thr Leu Ser Arg Gly Pro Ala
65                  70                  75                  80

Phe Pro Gly Met Gly Ser Glu Glu Leu Arg Leu Ala Ser Phe Tyr Asp
                85                  90                  95

Trp Pro Leu Thr Ala Glu Val Pro Pro Glu Leu Leu Ala Ala Ala Gly
            100                 105                 110

Phe Phe His Thr Gly His Gln Asp Lys Val Arg Cys Phe Phe Cys Tyr
        115                 120                 125

Gly Gly Leu Gln Ser Trp Lys Arg Gly Asp Asp Pro Trp Thr Glu His
    130                 135                 140

Ala Lys Trp Phe Pro Ser Cys Gln Phe Leu Leu Arg Ser Lys Gly Arg
145                 150                 155                 160

Asp Phe Val His Ser Val Gln Glu Thr His Ser Gln Leu Leu Gly Ser
                165                 170                 175

Trp Asp Pro Trp Glu Glu Pro Glu Asp Ala Ala Pro Val Ala Pro Ser
```

| | | | | 180 | | | | 185 | | | | 190 | | |
|---|---|---|---|---|---|---|---|---|---|---|---|---|---|---|

Val Pro Ala Ser Gly Tyr Pro Glu Leu Pro Thr Pro Arg Arg Glu Val
        195                  200                  205

Gln Ser Glu Ser Ala Gln Glu Pro Gly Gly Val Ser Pro Ala Glu Ala
        210                  215                  220

Gln Arg Ala Trp Trp Val Leu Glu Pro Pro Gly Ala Arg Asp Val Glu
225                  230                  235                  240

Ala Gln Leu Arg Arg Leu Gln Glu Glu Arg Thr Cys Lys Val Cys Leu
                245                  250                  255

Asp Arg Ala Val Ser Ile Val Phe Val Pro Cys Gly His Leu Val Cys
        260                  265                  270

Ala Glu Cys Ala Pro Gly Leu Gln Leu Cys Pro Ile Cys Arg Ala Pro
        275                  280                  285

Val Arg Ser Arg Val Arg Thr Phe Leu Ser
        290                  295

<210> SEQ ID NO 3
<211> LENGTH: 751
<212> TYPE: DNA
<213> ORGANISM: Homo sapiens

<400> SEQUENCE: 3

```
gggcagatcc tgggccagct gcggcccctg acagaggagg aagaggagga gggcgccggg    60
gccaccttgt ccagggggcc tgccttcccc ggcatgggct ctgaggagtt gcgtctggcc   120
tccttctatg actggccgct gactgctgag gtgccacccg agctgctggc tgctgccggc   180
ttcttccaca caggccatca ggacaaggtg aggtgcttct tctgctatgg gggcctgcag   240
agctggaagc gcggggacga cccctggacg gagcatgcca gtggttccc cagctgtcag   300
ttcctgctcc ggtcaaaagg aagagacttt gtccacagtg tgcaggagac tcactcccag   360
ctgctgggct cctgggaccc gtgggaagaa ccggaagacg cagcccctgt ggccccctcc   420
gtccctgcct ctgggtaccc tcgagctgcc acacccagg agagaggtcc agtctgaaag   480
tgcccaggag ccaggagggg tcagtccagc cgaggcccag agggcgtggt gggttcttga   540
gcccccagga gccagggatg tggaggcgca gctgcggcgg ctgcaggagg agaggacgtg   600
caaggtgtgc ctggaccgcg ccgtgtccat cgtctttgtg ccgtgcggcc acctggtctg   660
tgctgagtgt gcccccggcc tgcagctgtg ccccatctgc agagccccg tccgcagccg   720
cgtgcgcacc ttcctgtcct aggccaggtg c                                  751
```

<210> SEQ ID NO 4
<211> LENGTH: 246
<212> TYPE: PRT
<213> ORGANISM: Homo sapiens

<400> SEQUENCE: 4

Gly Gln Ile Leu Gly Gln Leu Arg Pro Leu Thr Glu Glu Glu Glu Glu
1                5                      10                  15

Glu Gly Ala Gly Ala Thr Leu Ser Arg Gly Pro Ala Phe Pro Gly Met
                20                  25                  30

Gly Ser Glu Glu Leu Arg Leu Ala Ser Phe Tyr Asp Trp Pro Leu Thr
        35                  40                  45

Ala Glu Val Pro Pro Glu Leu Leu Ala Ala Ala Gly Phe Phe His Thr
        50                  55                  60

Gly His Gln Asp Lys Val Arg Cys Phe Phe Cys Tyr Gly Gly Leu Gln
65                  70                  75                  80

Ser Trp Lys Arg Gly Asp Asp Pro Trp Thr Glu His Ala Lys Trp Phe
            85                  90                  95

Pro Ser Cys Gln Phe Leu Leu Arg Ser Lys Gly Arg Asp Phe Val His
        100                 105                 110

Ser Val Gln Glu Thr His Ser Gln Leu Leu Gly Ser Trp Asp Pro Trp
        115                 120                 125

Glu Glu Pro Glu Asp Ala Ala Pro Val Ala Pro Ser Val Pro Ala Ser
    130                 135                 140

Gly Tyr Pro Glu Leu Pro Thr Pro Arg Arg Glu Val Gln Ser Glu Ser
145                 150                 155                 160

Ala Gln Glu Pro Gly Gly Val Ser Pro Ala Glu Ala Arg Ala Trp
            165                 170                 175

Trp Val Leu Glu Pro Pro Gly Ala Arg Asp Val Glu Ala Gln Leu Arg
        180                 185                 190

Arg Leu Gln Glu Glu Arg Thr Cys Lys Val Cys Leu Asp Arg Ala Val
        195                 200                 205

Ser Ile Val Phe Val Pro Cys Gly His Leu Val Cys Ala Glu Cys Ala
        210                 215                 220

Pro Gly Leu Gln Leu Cys Pro Ile Cys Arg Ala Pro Val Arg Ser Arg
225                 230                 235                 240

Val Arg Thr Phe Leu Ser
            245

<210> SEQ ID NO 5
<211> LENGTH: 1332
<212> TYPE: DNA
<213> ORGANISM: Homo sapiens

<400> SEQUENCE: 5
gaccccagag gccaccctgg ccacttccag aaagctgtgg gccctgggat actcccctcc      60
cagggtgtct ggtggcaggc ctgtgcctat ccctgctgtc cccagggtgg ccccggggg     120
tcaggagctc agaagggcc agctgggcat attctgagat tggccatcag cccccatttc     180
tgctgcaaac ctggtcagag ccagtgttcc ctccatggga cctaaagaca gtgccaagtg     240
cctgcaccgt ggaccacagc cgagccactg ggcagccggt gatggtccca cgcaggagcg     300
ctgtggaccc cgctctctgg gcagcccgtg cctaggcctg acacctgca gagcctggga     360
ccacgtggat gggcagatcc tgggccagct gcggcccctg acagaggagg aagaggagga     420
gggcgccggg gccaccttgt ccaggggcc tgccttcccc ggcatgggct ctgaggagtt     480
gcgtctggcc tccttctatg actggccgct gactgctgag gtgccacccg agctgctggc     540
tgctgccggc ttcttccaca caggccatca ggacaaggtg aggtgcttct tctgctatgg     600
gggcctgcag agctggaagc gcggggacga cccctggacg gagcatgcca agtggttccc     660
cagctgtcag ttcctgctcc ggtcaaaagg aagagacttt gtccacagtg tgcaggagac     720
tcactcccag ctgctgggct cctggacccc gtgggaagaa ccggaagacg cagcccctgt     780
ggccccctcc gtccctgcct ctgggtaccc tgagctgccc acacccagga gagaggtcca     840
gtctgaaagt gccaggagc aggagccagg ggatgtggag gcgcagctgc ggcggctgca     900
ggaggagagg acgtgcaagg tgtgcctgga ccgcgccgtg tccatcgtct ttgtgccgtg     960
cggccacctg gtctgtgctg agtgtgcccc cggcctgcag ctgtgcccca tctgcagagc    1020
ccccgtccgc agccgcgtgc gcaccttcct gtcctaggcc aggtgccatg gccgcccagg    1080
tgggctgcag agtgggctcc ctgccccctct ctgcctgttc tggactgtgt tctgggcctg    1140

-continued

```
ctgaggatgg cagagctggt gtccatccag cactgaccag ccctgattcc ccgaccaccg    1200
cccagggtgg agaaggaggc ccttgcttgg cgtgggggat ggcttaactg tacctgtttg    1260
gatgcttctg aatagaaata aagtgggttt tccctggagg tacccagcag cctgaaaaaa    1320
aaaaaaaaaa aa                                                        1332
```

<210> SEQ ID NO 6
<211> LENGTH: 280
<212> TYPE: PRT
<213> ORGANISM: Homo sapiens

<400> SEQUENCE: 6

```
Met Gly Pro Lys Asp Ser Ala Lys Cys Leu His Arg Gly Pro Gln Pro
1               5                   10                  15

Ser His Trp Ala Ala Gly Asp Gly Pro Thr Gln Glu Arg Cys Gly Pro
                20                  25                  30

Arg Ser Leu Gly Ser Pro Val Leu Gly Leu Asp Thr Cys Arg Ala Trp
            35                  40                  45

Asp His Val Asp Gly Gln Ile Leu Gly Gln Leu Arg Pro Leu Thr Glu
        50                  55                  60

Glu Glu Glu Glu Glu Gly Ala Gly Ala Thr Leu Ser Arg Gly Pro Ala
65                  70                  75                  80

Phe Pro Gly Met Gly Ser Glu Glu Leu Arg Leu Ala Ser Phe Tyr Asp
                85                  90                  95

Trp Pro Leu Thr Ala Glu Val Pro Pro Glu Leu Leu Ala Ala Ala Gly
            100                 105                 110

Phe Phe His Thr Gly His Gln Asp Lys Val Arg Cys Phe Phe Cys Tyr
        115                 120                 125

Gly Gly Leu Gln Ser Trp Lys Arg Gly Asp Asp Pro Trp Thr Glu His
    130                 135                 140

Ala Lys Trp Phe Pro Ser Cys Gln Phe Leu Leu Arg Ser Lys Gly Arg
145                 150                 155                 160

Asp Phe Val His Ser Val Gln Glu Thr His Ser Gln Leu Leu Gly Ser
                165                 170                 175

Trp Asp Pro Trp Glu Glu Pro Glu Asp Ala Ala Pro Val Ala Pro Ser
            180                 185                 190

Val Pro Ala Ser Gly Tyr Pro Glu Leu Pro Thr Pro Arg Arg Glu Val
        195                 200                 205

Gln Ser Glu Ser Ala Gln Glu Pro Gly Ala Arg Asp Val Glu Ala Gln
    210                 215                 220

Leu Arg Arg Leu Gln Glu Glu Arg Thr Cys Lys Val Cys Leu Asp Arg
225                 230                 235                 240

Ala Val Ser Ile Val Phe Val Pro Cys Gly His Leu Val Cys Ala Glu
                245                 250                 255

Cys Ala Pro Gly Leu Gln Leu Cys Pro Ile Cys Arg Ala Pro Val Arg
            260                 265                 270

Ser Arg Val Arg Thr Phe Leu Ser
        275                 280
```

<210> SEQ ID NO 7
<211> LENGTH: 687
<212> TYPE: DNA
<213> ORGANISM: Homo sapiens

<400> SEQUENCE: 7

```
gggcagatcc tgggccagct gcggcccctg acagaggagg aagaggagga gggcgccggg    60
gccaccttgt ccaggggggcc tgccttcccc ggcatgggct ctgaggagtt gcgtctggcc  120
tccttctatg actggccgct gactgctgag gtgccacccg agctgctggc tgctgccggc  180
ttcttccaca caggccatca ggacaaggtg aggtgcttct tctgctatgg gggcctgcag  240
agctggaagc gcggggacga cccctggacg gagcatgcca agtggttccc cagctgtcag  300
ttcctgctcc ggtcaaaagg aagagacttt gtccacagtg tgcaggagac tcactcccag  360
ctgctgggct cctgggaccc gtgggaagaa ccggaagacg cagcccctgt ggcccccctcc  420
gtccctgcct ctgggtaccc tgagctgccc acacccagga gagaggtcca gtctgaaagt  480
gcccaggagc caggagccag ggatgtggag cgcagctgc ggcggctgca ggaggagagg    540
acgtgcaagg tgtgcctgga ccgcgccgtg tccatcgtct ttgtgccgtg cggccacctg  600
gtctgtgctg agtgtgcccc cggcctgcag ctgtgcccca tctgcagagc cccgtccgc   660
agccgcgtgc gcaccttcct gtcctag                                       687
```

<210> SEQ ID NO 8
<211> LENGTH: 228
<212> TYPE: PRT
<213> ORGANISM: Homo sapiens
<400> SEQUENCE: 8

```
Gly Gln Ile Leu Gly Gln Leu Arg Pro Leu Thr Glu Glu Glu Glu
1               5                   10                  15

Glu Gly Ala Gly Ala Thr Leu Ser Arg Gly Pro Ala Phe Pro Gly Met
            20                  25                  30

Gly Ser Glu Glu Leu Arg Leu Ala Ser Phe Tyr Asp Trp Pro Leu Thr
        35                  40                  45

Ala Glu Val Pro Pro Glu Leu Leu Ala Ala Ala Gly Phe Phe His Thr
    50                  55                  60

Gly His Gln Asp Lys Val Arg Cys Phe Phe Cys Tyr Gly Gly Leu Gln
65                  70                  75                  80

Ser Trp Lys Arg Gly Asp Asp Pro Trp Thr Glu His Ala Lys Trp Phe
                85                  90                  95

Pro Ser Cys Gln Phe Leu Leu Arg Ser Lys Gly Arg Asp Phe Val His
            100                 105                 110

Ser Val Gln Glu Thr His Ser Gln Leu Leu Gly Ser Trp Asp Pro Trp
        115                 120                 125

Glu Glu Pro Glu Asp Ala Ala Pro Val Ala Pro Ser Val Pro Ala Ser
    130                 135                 140

Gly Tyr Pro Glu Leu Pro Thr Pro Arg Arg Glu Val Gln Ser Glu Ser
145                 150                 155                 160

Ala Gln Glu Pro Gly Ala Arg Asp Val Glu Ala Gln Leu Arg Arg Leu
                165                 170                 175

Gln Glu Glu Arg Thr Cys Lys Val Cys Leu Asp Arg Ala Val Ser Ile
            180                 185                 190

Val Phe Val Pro Cys Gly His Leu Val Cys Ala Glu Cys Ala Pro Gly
        195                 200                 205

Leu Gln Leu Cys Pro Ile Cys Arg Ala Pro Val Arg Ser Arg Val Arg
    210                 215                 220

Thr Phe Leu Ser
225
```

<210> SEQ ID NO 9

<211> LENGTH: 1332
<212> TYPE: DNA
<213> ORGANISM: Homo sapiens

<400> SEQUENCE: 9

```
gacccagag gccaccctgg ccacttccag aaagctgtgg gccctgggat actccctcc      60
cagggtgtct ggtggcaggc ctgtgcctat ccctgctgtc cccagggtgg gccccggggg    120
tcaggagctc cagaagggcc agctgggcat attctgagat tggccatcag cccccatttc    180
tgctgcaaac ctggtcagag ccagtgttcc ctccatggga cctaaagaca gtgccaagtg    240
cctgcaccgt ggaccacagc cgagccactg ggcagccggt gatggtccca cgcaggagcg    300
ctgtggaccc cgctctctgg gcagccctgt cctaggcctg acacctgca gagcctggga     360
ccacgtggat gggcagatcc tgggccagct gcggcccctg acagaggagg aagaggagga    420
gggcgccggg gccaccttgt ccaggggggcc tgccttcccc ggcatgggct ctgaggagtt    480
gcgtctggcc tccttctatg actggccgct gactgctgag gtgccacccg agctgctggc    540
tgctgccggc ttcttccaca caggccatca ggacaaggtg aggtgcttct ctgctatgg     600
gggcctgcag agctggaagc gcggggacga cccctggacg gagcatgcca agtggttccc    660
cagctgtcag ttcctgctcc ggtcaaaagg aagagacttt gtccacagtg tgcaggagac    720
tcactcccag ctgctgggct cctgggaccc gtgggaagaa ccggaagacg cagcccctgt    780
ggcccccctcc gtccctgcct ctgggtaccc tgagctgccc acaccaggga gagaggtcca    840
gtctgaaagt gcccaggagc caggagccag ggatgtggag gcgcagctgc ggcggctgca    900
ggaggagagg acgtgcaagg tgtgcctgga ccgcgccgtg tccatcgtct ttgtgccgtg    960
cggccacctg gtctgtgctg agtgtgcccc cggcctgcag ctggccccca tctgcagagc    1020
ccccgtccgc agccgcgtgc gcaccttcct gtcctaggcc aggtgccatg gccggccagg    1080
tgggctgcag agtgggctcc ctgccctct ctgcctgttc tggactgtgt tctgggcctg    1140
ctgaggatgg cagagctggt gtccatccag cactgaccag ccctgattcc ccgaccaccg    1200
cccagggtgg agaaggaggc ccttgcttgg cgtgggggat ggcttaactg tacctgtttg    1260
gatgcttctg aatagaaata aagtgggttt tccctggagg tacccagcag cctgaaaaaa    1320
aaaaaaaaaa aa                                                        1332
```

<210> SEQ ID NO 10
<211> LENGTH: 280
<212> TYPE: PRT
<213> ORGANISM: Homo sapiens

<400> SEQUENCE: 10

```
Met Gly Pro Lys Asp Ser Ala Lys Cys Leu His Arg Gly Pro Gln Pro
1               5                   10                  15

Ser His Trp Ala Ala Gly Asp Gly Pro Thr Gln Glu Arg Cys Gly Pro
            20                  25                  30

Arg Ser Leu Gly Ser Pro Val Leu Gly Leu Asp Thr Cys Arg Ala Trp
        35                  40                  45

Asp His Val Asp Gly Gln Ile Leu Gly Gln Leu Arg Pro Leu Thr Glu
    50                  55                  60

Glu Glu Glu Glu Glu Gly Ala Gly Ala Thr Leu Ser Arg Gly Pro Ala
65                  70                  75                  80

Phe Pro Gly Met Gly Ser Glu Glu Leu Arg Leu Ala Ser Phe Tyr Asp
                85                  90                  95

Trp Pro Leu Thr Ala Glu Val Pro Pro Glu Leu Leu Ala Ala Ala Gly
```

```
                    100                 105                 110
Phe Phe His Thr Gly His Gln Asp Lys Val Arg Cys Phe Phe Cys Tyr
            115                 120                 125

Gly Gly Leu Gln Ser Trp Lys Arg Gly Asp Asp Pro Trp Thr Glu His
        130                 135                 140

Ala Lys Trp Phe Pro Ser Cys Gln Phe Leu Leu Arg Ser Lys Gly Arg
145                 150                 155                 160

Asp Phe Val His Ser Val Gln Glu Thr His Ser Gln Leu Leu Gly Ser
                165                 170                 175

Trp Asp Pro Trp Glu Glu Pro Glu Asp Ala Ala Pro Val Ala Pro Ser
            180                 185                 190

Val Pro Ala Ser Gly Tyr Pro Glu Leu Pro Thr Pro Arg Arg Glu Val
        195                 200                 205

Gln Ser Glu Ser Ala Gln Glu Pro Gly Ala Arg Asp Val Glu Ala Gln
    210                 215                 220

Leu Arg Arg Leu Gln Glu Glu Arg Thr Cys Lys Val Cys Leu Asp Arg
225                 230                 235                 240

Ala Val Ser Ile Val Phe Val Pro Cys Gly His Leu Val Cys Ala Glu
                245                 250                 255

Cys Ala Pro Gly Leu Gln Leu Ala Pro Ile Cys Arg Ala Pro Val Arg
            260                 265                 270

Ser Arg Val Arg Thr Phe Leu Ser
        275                 280

<210> SEQ ID NO 11
<211> LENGTH: 27
<212> TYPE: DNA
<213> ORGANISM: Artificial Sequence
<220> FEATURE:
<223> OTHER INFORMATION: Single strand DNA oligonucleotide

<400> SEQUENCE: 11
ggggaattct ggtcagagcc agtgttc                                        27

<210> SEQ ID NO 12
<211> LENGTH: 24
<212> TYPE: DNA
<213> ORGANISM: Artificial Sequence
<220> FEATURE:
<223> OTHER INFORMATION: Single strand DNA oligonucleotide

<400> SEQUENCE: 12
gggggatccg gagcccactc tgca                                           24

<210> SEQ ID NO 13
<211> LENGTH: 71
<212> TYPE: DNA
<213> ORGANISM: Artificial Sequence
<220> FEATURE:
<223> OTHER INFORMATION: Single strand DNA oligonucleotide

<400> SEQUENCE: 13
gggggatccc taggacagga aggtgcgcac gcggctgcgg acggggctc tgccagatgg    60 gggccagctg c                                                        71
```

COMPOSITIONS AND METHODS FOR INDUCING THROMBOPOIESIS

RELATED APPLICATION

This application is a division of U.S. patent application Ser. No. 14/534,394 filed on Nov. 6, 2014, which claims the benefit of priority under 35 USC § 119(e) of U.S. Provisional Patent Application No. 61/900,417 filed Nov. 6, 2013, the contents of which are incorporated herein by reference in their entirety.

SEQUENCE LISTING STATEMENT

The ASCII file, entitled 77498SequenceListing.txt, created on Apr. 23, 2019, comprising 20,484 bytes, submitted concurrently with the filing of this application is incorporated herein by reference.

FIELD AND BACKGROUND OF THE INVENTION

The present invention, in some embodiments thereof, relates to compositions and methods for inducing thrombopoiesis.

Platelets are circulating cell-derived fragments that are required for the maintenance of hemostasis. These small, anucleate fragments represent the first line of defense against hemorrhage following vascular injury, and are crucial for blood coagulation. Thrombopoiesis is the complex process of platelet production from megakaryocytes (MKs), and even to date is incompletely understood. Functional platelets are the terminal differentiation product of this process. Specifically, in the bone marrow (BM), MKs give rise to circulating platelets through commitment of the multipotent hematopoietic stem cell to the MK lineage, proliferation of the progenitors and terminal differentiation of MKs by blebbing of their membrane and production of platelet fragments. This process is characterized by DNA endoreplication, followed by cytoplasmic maturation and expansion. Platelets form as the fully mature MK develops cytoplasmic extensions, or pseudopodial protrusions, that extend in proximity to sinusoidal endothelial cells (Deutsch V R and Tomer A. Br J Haematol. 161(6):778-93 (2013), Tvassoli and Aoki, Blood Cells, 15:3-14 (1989)). Platelets bud from the ends of these protrusions and thereafter enter the circulation. The ability of MK to produce platelet buds is ultimately exhausted, and it undergoes terminal apoptosis.

A number of diseases, such as ITP and TTP, or conditions result in low levels or poor functioning of blood platelets. For example, pancytopenia and prolonged thrombocytopenia, which remain a significant clinical challenge for patients undergoing hematopoietic stem cell transplantation and high dose chemotherapy. Chemotherapy or irradiation-associated depletion of hematopoietic precursors in the BM results in hemorrhagic and life threatening infectious complications. Engraftment of transplanted cells or regeneration of normal hematopoiesis and blood count recovery is usually accomplished within 2 to 5 weeks. The reason for this delay has been attributed to insufficient MK precursors in the grafts[48].

Currently available treatments for thrombocytopenia and related conditions include, for example, corticosteroids, IVIG, splenectomy, and whole blood or platelet transfusion, methods which are either palliative and non-specific, or drastic and expensive. Platelets for such procedures are obtained by plateletphoresis from normal donors. However the efficiency of such costly transfusions can be limited since platelets have a relatively short shelf-life of about 5 days. Furthermore, patients are often refractory to subsequent transfusions. Injections of Thrombopoietin (TPO), the physiologic regulator of thrombopoiesis, and TPO mimetics to increase platelet count has not been clinically effective due to a lag period before the level of platelets was affected.

Thus, there remains a need for new and improved methods for stimulating or enhancing the production of platelets.

The IAP family of proteins has been shown to inhibit apoptosis induced by a variety of stimuli mainly by binding and inhibiting specific caspases[25]. Eight human IAPs have been identified to date: c-IAP1, c-IAP2, NAIP, Survivin, XIAP, Bruce, ILP-2 and Livin.

Livin, also known as baculoviral IAP repeat-containing 7; BIRC7, KIAP, ML-IAP and Livin inhibitor-of-apoptosis, contains a single baculovirus IAP repeats (BIR) domain at the N-terminus and a carboxy-terminal RING domain[29-31]. The BIR domain was shown to play a role in the anti-apoptotic function of IAPs[26,27]. Livin encodes two highly similar splicing variants, termed Livin α and β that differ only in 18 amino acids located between the BIR and the RING domains, which are present in the α but not in the β isoform. Following apoptotic stimuli, both Livin isoforms α and β undergo a specific proteolytic cleavage that trims the 52 amino acids at the N-terminus of Livin. From each isoform a truncated C-terminal Livin is thus produced, of approximately 30 kDa (also termed p30) and 28 kDa (also termed p28), respectively, containing the full BIR and RING domains (Ashhab, Y. et al. FEBS letters, 495: 56-60 (2001)). These truncated forms of Livin are collectively referred to as tLivin. Recent reports show that tLivin is not only devoid of Livin anti-apoptotic activity but also acquires a pro-apoptotic effect[32,33]. Thus, Livin is unique among the IAP members, exerting both anti-apoptotic and pro-apoptotic activities making it a regulator of apoptosis rather than anti-apoptotic protein[32,33].

U.S. Pat. No. 7,517,949 discloses Livin-derived peptides with pro-apoptotic activity. Specifically provided are peptides p30-Livin α and p28-Livin β, derived from Livin α and β truncation, respectively, as well as compositions thereof. These peptides display pro-apoptotic activity and as such are used for the enhancement and/or induction of apoptosis, as well as for the treatment of cancer.

ADDITIONAL RELATED ART

Abd El-Rahman et al. Blood (ASH Annual Meeting Abstracts), 120: Abstract 3297 (2012).

Abd El-Rahman et al. Blood (ASH Annual Meeting Abstracts), 112: Abstract 1842 (2008).

Abd El-Rahman et al. Blood (ASH Annual Meeting Abstracts), 108: Abstract 4301 (2006).

SUMMARY OF THE INVENTION

According to an aspect of some embodiments of the present invention there is provided a method of inducing thrombopoiesis, the method comprising contacting stem cells with a differentiation potential towards platelets or hematopoietic progenitor cells derived therefrom with Livin, thereby inducing thrombopoiesis.

According to an aspect of some embodiments of the present invention there is provided a method of inducing thrombopoiesis, the method comprising contacting cells with a differentiation potential towards platelets with tLivin, thereby inducing thrombopoiesis.

According to some embodiments of the invention the cells with differentiation potential towards platelets are selected from the group consisting of stem cells with a differentiation potential towards platelets, hematopoietic progenitor cells derived therefrom, and LAMA-84 cells.

According to some embodiments of the invention the method further comprises contacting the cells with a platelet production stimulating factor.

According to some embodiments of the invention the contacting is effected ex-vivo or in-vitro.

According to some embodiments of the invention the contacting is effected in-vivo.

According to some embodiments of the invention there is provided an isolated population of cells generated according to the method.

According to an aspect of some embodiments of the present invention there is provided an isolated population of cells comprising stem cells with a differentiation potential towards platelets or hematopoietic progenitor cells derived therefrom and a nucleic acid construct comprising a polynucleotide encoding Livin.

According to an aspect of some embodiments of the present invention there is provided an isolated population of cells comprising cells with a differentiation potential towards platelets and a nucleic acid construct comprising a polynucleotide encoding tLivin.

According to some embodiments of the invention there is provided a method of inducing thrombopoiesis in a subject in need thereof, the method comprising administering to the subject a therapeutically effective amount of the cells, thereby inducing thrombopoiesis in the subject.

According to some embodiments of the invention there is provided a method of treating thrombocytopenia in a subject, the method comprising administering to the subject a therapeutically effective amount of the cells, thereby treating the subject.

According to an aspect of some embodiments of the present invention there is provided a method of inducing thrombopoiesis in a subject in need thereof, the method comprising administering to the subject a therapeutically effective amount of Livin, thereby inducing thrombopoiesis in the subject.

According to an aspect of some embodiments of the present invention there is provided a method of treating thrombocytopenia in a subject, the method comprising administering to the subject a therapeutically effective amount of Livin, thereby treating the subject.

According to some embodiments of the invention the method further comprises administering to the subject a platelet production stimulating factor.

According to some embodiments of the invention the subject is treated with an anti thrombocytopenia therapy.

According to some embodiments of the invention the anti thrombocytopenia therapy is a platelet production stimulating factor.

According to some embodiments of the invention the subject is diagnosed with thrombocytopenia.

According to some embodiments of the invention the subject suffers from or is at a risk of platelet reduction associated with exposure to radiation or chemotherapy.

According to an aspect of some embodiments of the present invention there is provided an article of manufacture identified for inducing thrombopoiesis comprising a packaging material packaging Livin and a platelet production stimulating factor.

According to some embodiments of the invention the Livin and the platelet production stimulating factor are packaged in separate containers.

According to some embodiments of the invention the Livin and the platelet production stimulating factor are in a co-formulation.

According to an aspect of some embodiments of the present invention there is provided a pharmaceutical composition comprising as active ingredients Livin and a platelet production stimulating factor and a pharmaceutically acceptable carrier or diluent.

According to some embodiments of the invention the hematopoietic progenitor cells comprise megakaryocytes.

According to some embodiments of the invention the stem cells with a differentiation potential towards platelets or hematopoietic progenitor cells are comprised in a biological sample.

According to some embodiments of the invention the biological sample is selected from the group consisting of cord blood, peripheral blood (PB), peripheral blood mononuclear cells (PBMCs) and bone marrow.

According to some embodiments of the invention the biological sample comprises PBMCs.

According to some embodiments of the invention the Livin is tLivin.

According to some embodiments of the invention the tLivin is p30-Livin α.

According to some embodiments of the invention the tLivin is p28-Livin β.

According to some embodiments of the invention the Livin is Livin α isoform or a Livin β isoform.

According to some embodiments of the invention the Livin is administered in a formulation suitable for cell penetration.

According to some embodiments of the invention the tLivin is administered in a formulation suitable for cell penetration. According to some embodiments of the invention the formulation is selected from the group consisting of a liposome, a nanoparticle, a viral vector or a cell penetrating peptide.

According to some embodiments of the invention the platelet production stimulating factor is selected from the group consisting of thrombopoietin (TPO), TPO agonist, stem cell factor (SCF) and Phorbol myristate acetate (PMA).

According to some embodiments of the invention the stem cells are embryonic stem cells (ESC) or induced pluripotent stem cells (iPS).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
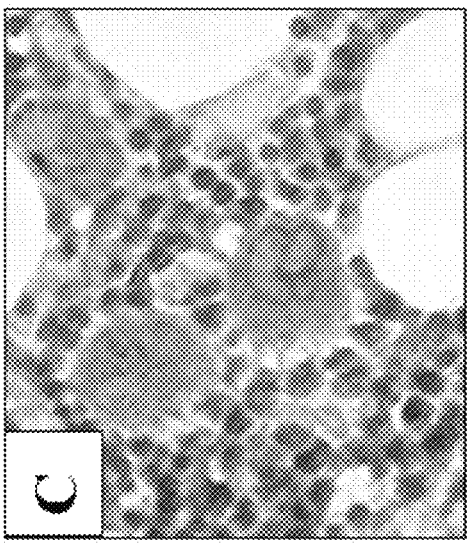
Figure 1B:
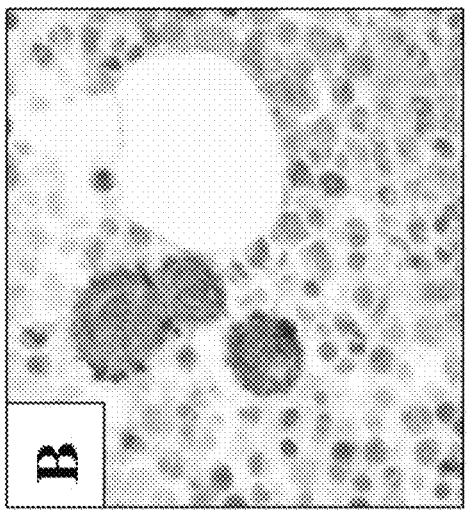
Figure 1C:
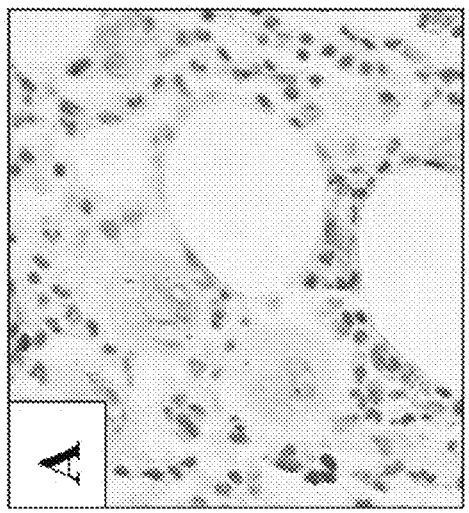
Figure 1D:
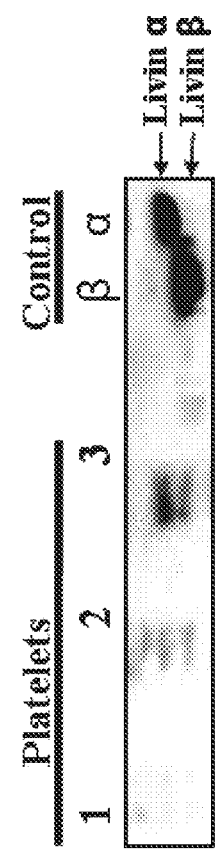

FIGS. 1A-1D demonstrate positive Livin expression in human MKs and platelets. FIGS. 1A-1C are immunohistochemical photomicrographs (magnification ×20) stained by anti-Livin specific antibody followed by secondary goat anti-mouse Ig horseradish peroxidase-conjugated antibody and counter stained with hematoxylin. FIG. 1A is a negative control showing no staining of a bone marrow (BM) sample with secondary antibody and counter staining with hematoxylin. FIG. 1B shows positive staining of mature MKs with anti-Livin specific antibody in a BM sample obtained from a healthy subject. FIG. 1C shows positive staining of mature MKs with anti-Livin specific antibody in a BM sample obtained from a patient with immune thrombocytopenic purpura (ITP). Note the distinct positive staining patterns of Livin in this sample and the sample shown in FIG. 1B. FIG. 1D is a Western blot photograph demonstrating expression of Livin protein in platelets derived from platelet concentrate. Lanes 1-3 show positive expression of Livin α and Livin β in immunopercipitated platelet concentrates extracted from blood of three distinct healthy donors. Control Lanes (beta and alpha) show positive expression of Livin α and Livin β overexpressed in LAMA-84 cells by transient transfection.

Figure 2D:
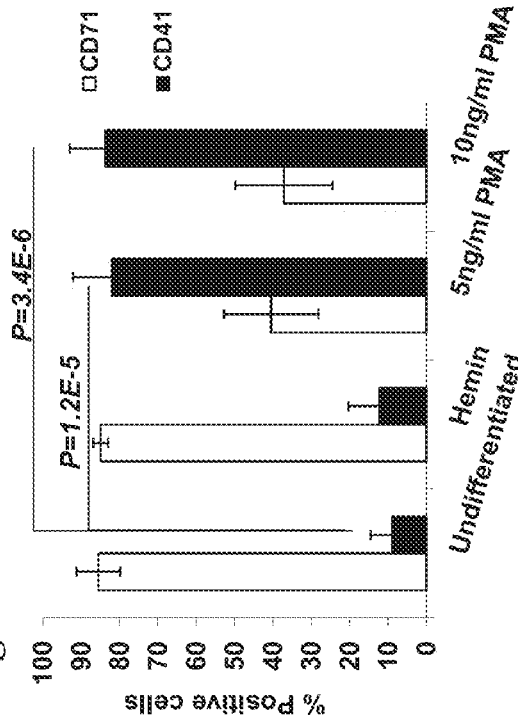
Figure 2E:
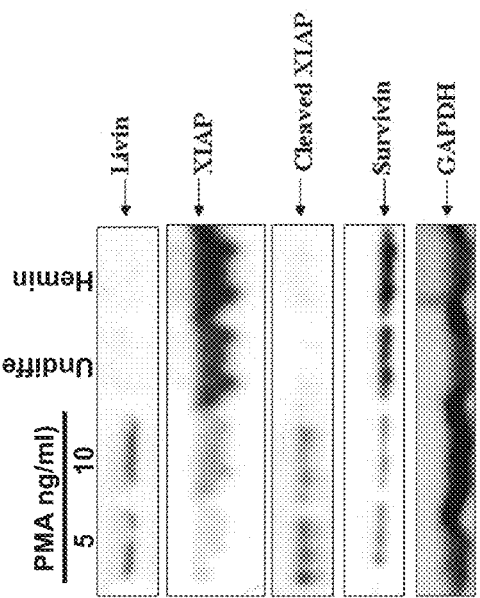
Figure 2A:
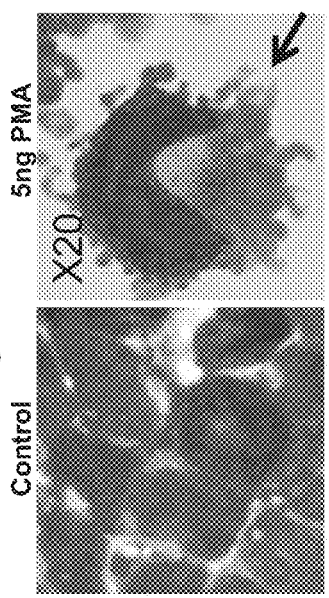
Figure 2B:
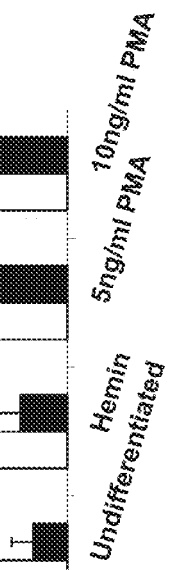
Figure 2B:
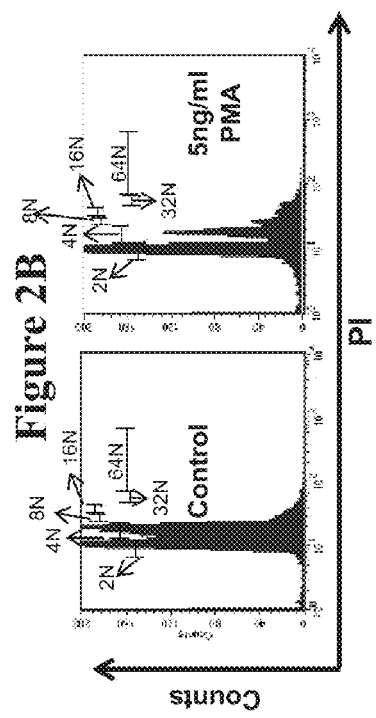
Figure 2C:
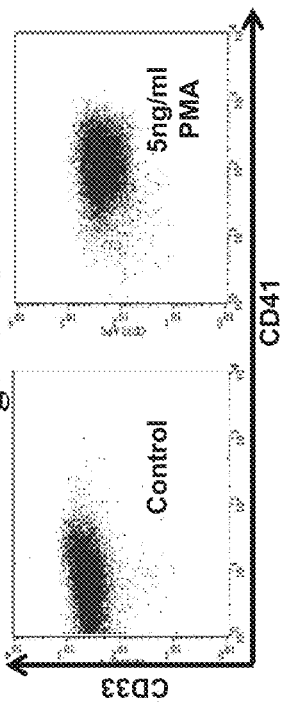

FIGS. 2A-2E show differentiation induction of LAMA-84 cells ($0.5 \times 10^6$/ml) toward the MK lineage by PMA (1.25-10 ng/ml) or towards the erythroid lineage by Hemin (50 μM). Cell cultures were harvested and analyzed 4 days following treatment. FIG. 2A shows histological photomicrographs stained by May-Grunwald Giemsa of cytospin preparations obtained from PMA treated (right plot) and untreated (left plot) cells (magnification ×20). Proplatelet projections in the PMA treated cells are indicated by a black arrow. FIG. 2B shows flow cytometry histograms representing nuclear ploidy of untreated cell cultures (left plot) and cell cultures treated with PMA (right plot). Cells were stained with propidium iodide (PI, 50 μg/ml) and analyzed according to M1=2N, M2=4N, M3=8N, M4=16N, M5=32N, M6=64N. FIG. 2C depicts flow cytometry dot plots analyzing CD33 (Myeloid marker) vs. CD41 (MK marker) expression in double stained PMA treated (right plot) and untreated (left plot) cells. FIG. 2D is a bar graph demonstrating the percentage of CD41 (MK marker) or CD71 (un-differentiated, early erythroid cell marker) positively stained cells as evaluated by flow cytometry. Cells were untreated or treated with PMA or with Hemin as indicated in the plot. FIG. 2E shows Western blot photographs demonstrating protein levels of Livin, Survivin, XIAP, and cleaved XIAP in PMA treated and untreated cells. The house keeping gene GAPDH expression is presented as positive control.

Figure 3H:
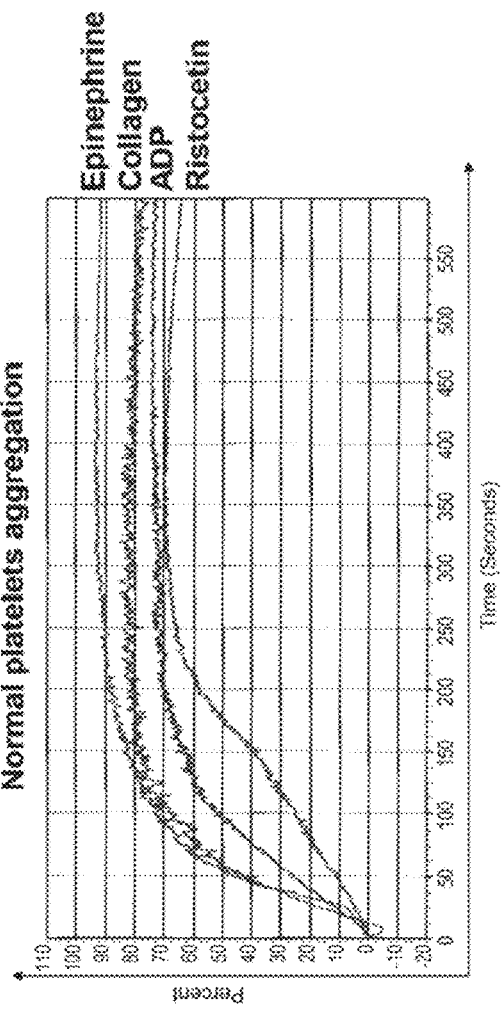
Figure 3I:
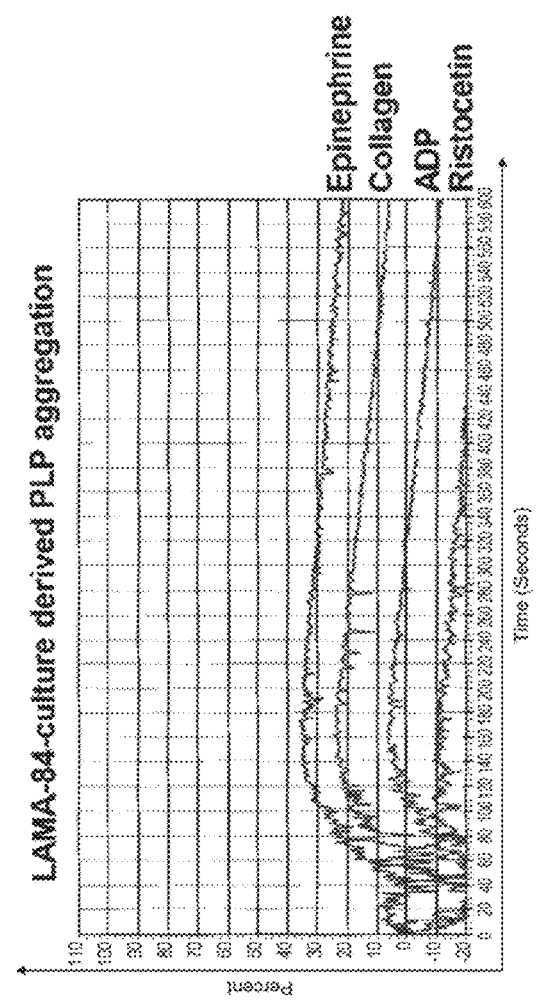

FIGS. 3A-3I show that differentiating LAMA-84 cells release functional platelet-like particles. FIG. 3A is a histological photomicrograph of culture derived particles obtained following 4 days treatment with PMA (5 ng/ml) stained with May-Gurnwald Giemsa (magnification ×20). Note that both mature platelets and pro-platelets were detected, indicated by arrows. FIGS. 3B-3G are dot plot analyses of cultures-derived particles as evaluated by flow cytometry. FIGS. 3B-3C show Forward Scatter (FSC) vs. Side Scatter (SSC) (FIG. 3B) and FSC vs. CD41 expression (FIG. 3C) in normal platelets from peripheral blood. This normal platelets sample was used as positive control for flow cytometry settings and gates definitions. FIGS. 3D-3E show FSC vs. SSC (FIG. 3D) and FSC vs. CD41 expression (FIG. 3E) in particles derived from untreated LAMA84 cultures. FIGS. 3F-3G show FSC vs. SSC (FIG. 3F) and of FSC vs. CD41 expression (FIG. 3G) in particles derived from LAMA84 cultures following 4 days treatment with PMA (5 ng/ml). FIG. 3H depicts aggregation percentages of positive control normal platelets in response to epinephrine, collagen, adenosine diphosphate (ADP) and ristocetin. FIG. 3I depicts aggregation percentages of PMA-treated LAMA-84 culture derived platelet-like particles in response to epinephrine, collagen, ADP and ristocetin.

Figure 4B:
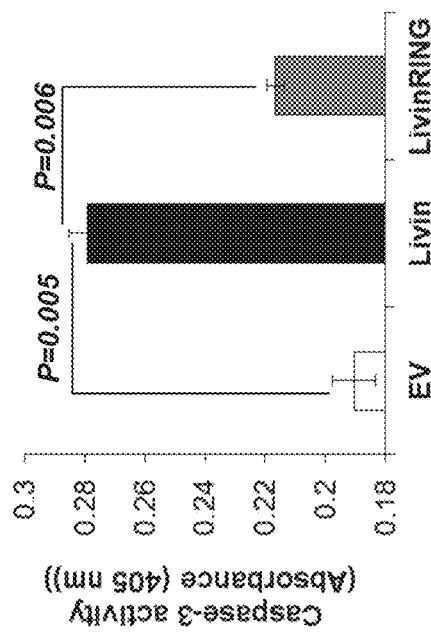
Figure 4D:
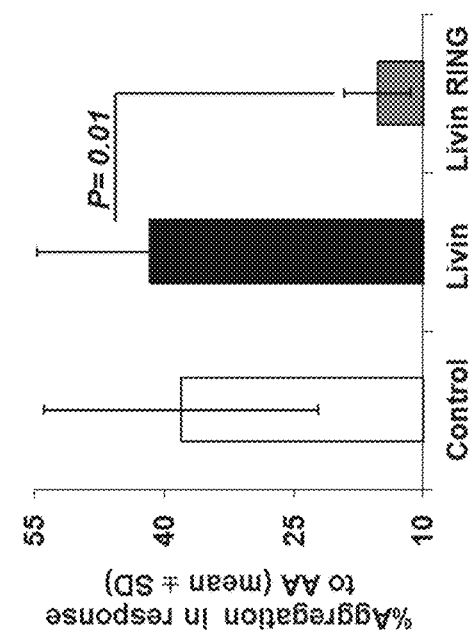
Figure 4A:
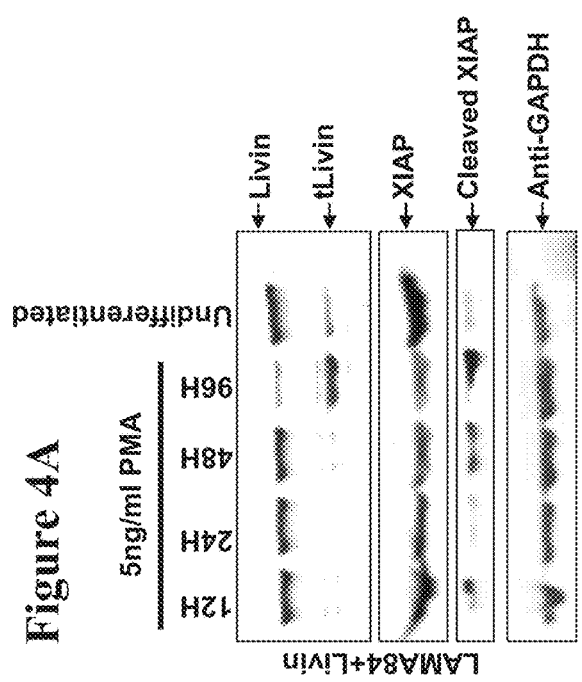
Figure 4C:
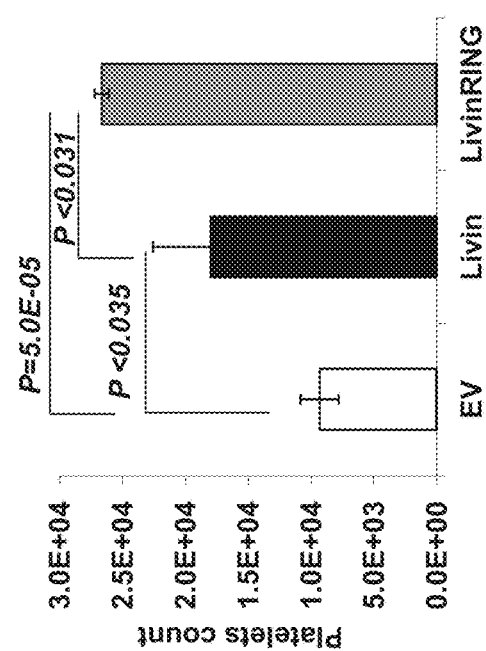

FIGS. 4A-4D exemplify that the pro-apoptotic activity of Livin is required for the generation of functional platelets. FIG. 4A shows Western blot photographs demonstrating the expression of Livin and XIAP proteins and their cleaved derivatives during differentiation of cells stably over-expressing wild-type Livin. Note the appearance of cleaved pro-apoptotic tLivin following 96 hours of exposure to PMA. The expression of the house keeping gene GAPDH is presented as positive control. FIG. 4B is a bar graph showing Caspase-3 activation as assessed through evaluation of caspase-3 enzyme activity (100 ng of protein) with Ac-DEVD-pNA in a colorimetric assay at day 4. FIG. 4C is a bar graph indicating the number of CD41+ culture-derived platelet-like particles collected at day 4 as evaluated by flow cytometry analysis. FIG. 4D is a bar graph demonstrating the percentage of platelet aggregation in response to arachidonic acid (AA) as evaluated by AGGRAM aggregometer.

Figure 5A:
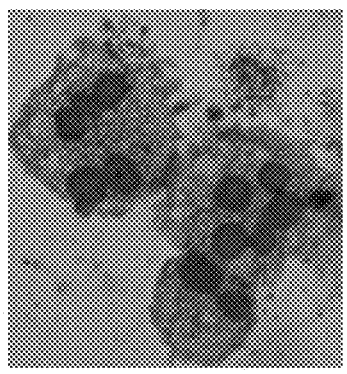
Figure 5B:
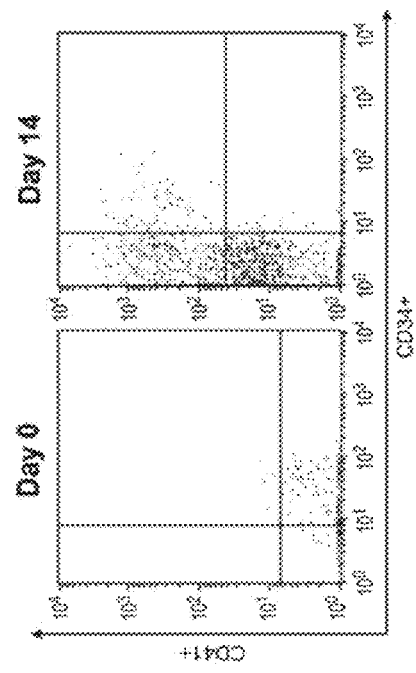
Figure 5C:
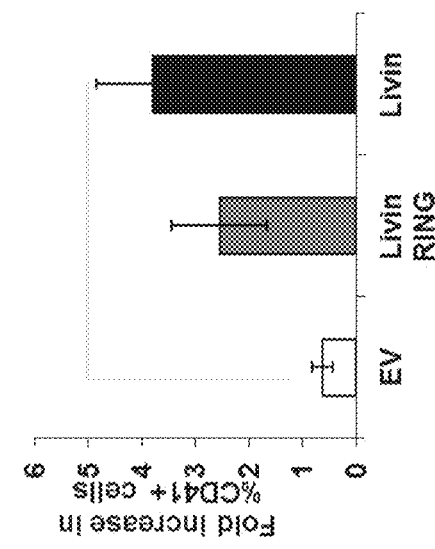
Figure 5D:
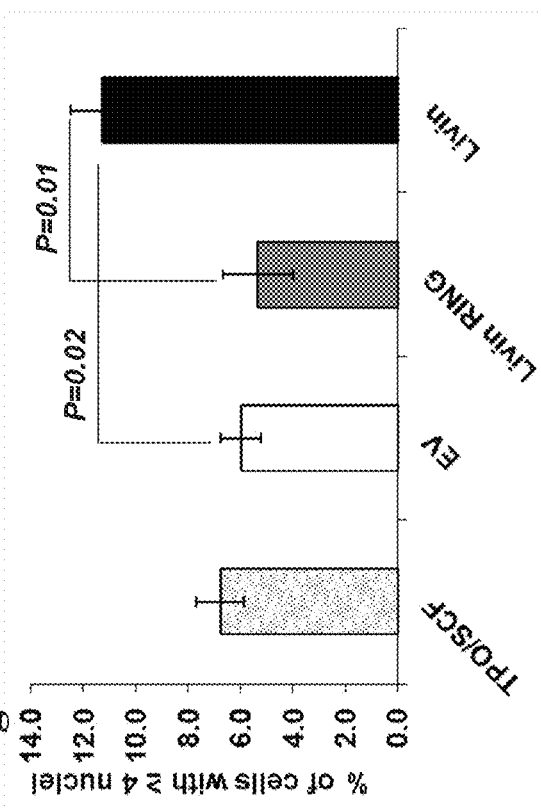
Figure 5E:
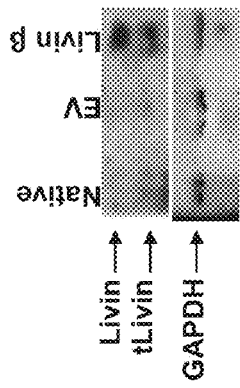

FIGS. 5A-5E illustrate that cord blood derived CD34+ cells over-expressing Livin show increased differentiation towards the MK lineage and higher nucleii number. FIG. 5A is a histological photomicrograph stained by May-Grunwald Giemsa showing polyploid MKs detected in cytospin preparation obtained from differentiated CD34+ cells infected with wild-type Livin (magnification ×60). FIG. 5B shows representative flow cytometry dot plots analyzing CD41 (MK marker) vs. CD34 expression in CD34+ cells infected with wild-type Livin before (left plot) and 14 days after (right plot) infection. FIG. 5C is a bar graph indicating fold increase over empty vector (EV) control in the percent of CD41+ cells in CD34+ cell cultures infected with either EV, wild-type Livin or Livin RING mutant (n=6). Data was evaluated by flow cyometry as presented in FIG. 5B. FIG. 5D is a bar graph demonstrating the percent of cells with high nuclei number (≥4 nuclei) in the differentiated CD34+ cell cultures infected with the above mentioned vectors, as evaluated by May-Grunwald Giemsa. FIG. 5E shows Western blot photographs demonstrating expression of Livin protein and its cleaved derivative (tLivin) in CD34+ cells infected with wild-type Livin. Control Lanes (Native and EV) show no expression of Livin and tLivin in undifferentiated CD34+ cells and CD34+ cells infected with EV, respectively. The expression of the house keeping gene GAPDH is presented as positive control.

FIGS. 6A-6D indicate that MKs induced from cord blood derived CD34+ cell cultures over-expressing wild-type Livin or LivinRmG mutant produce more platelets in comparison to control while only platelets produced by the over-expressing wild-type Livin are functional. FIG. 6A shows flow cytometry dot plots analyzing SSC vs. FSC and CD41 vs. FSC in cord blood platelets. This cord blood platelets sample was used as positive control for flow cytometry settings and gates definitions. FIG. 6B shows representative flow cytometry dot plots analyzing SSC vs. FSC and CD41 vs. FSC in platelets generated from CD34+ cultures infected with wild-type Livin. FIG. 6C is a bar graph indicating the fold increase over empty vector (EV) control in the percent of CD41+ platelets derived from CD34+ cells infected with either EV, wild-type Livin or Livin RING mutant. Data was evaluated by flow cyometry as presented in FIGS. 6A-6B. FIG. 6D shows flow cytometry histograms of CD62P expression in platelets derived from differentiated CD34+ cultures pre-incubated for 10 minutes at room temperature with Adenosine diphosphate (ADP) or Arachidonic Acid (AA).

FIGS. 7A-7E depict the effect of knock-down of Livin on platelets production and function in LAMA-84 cells treated with PMA and in cord blood derived CD34+ cells treated with SCF and TPO. Down-regulation of Livin expression was performed using pSUPER-Livin-2 (siRNA) or pSUPER-Luc (control) vectors. FIGS. 7A-7C demonstrate the effect of down-regulation of Livin expression in LAMA-84 cells. Cells were analyzed 4 days post treatment with PMA. FIG. 7A shows Western blot photographs demonstrating no expression of Livin protein in Livin knock-down cells. Note the down regulation of both Livin α and Livin expression. Control cells show positive expression of both Livin α and Livin β. The expression of the house keeping gene GAPDH is presented as positive control. FIG. 7B is a bar graph presenting the number of platelet-like particles (platelets count/LAMA-84 cells count) in control and Livin knock-down cells. FIG. 7C is a bar graph presenting aggregation induced by various agonists in control and in Livin knock-down LAMA-84 cells. FIGS. 7D-7E demonstrate the effect of down-regulation of Livin expression in CD34+ cells treated with SCF and TPO. Cells were analyzed on day 14 of differentiation. FIG. 7D is a bar graph demonstrating the percent of cells with high nuclei number (≥4 nuclei) in the differentiated CD34+ cell cultures, as evaluated by May-Grunwald Giemsa.

FIG. 7E shows flow cytometry histograms of CD62P expression in platelets derived from control and Livin knock-down differentiated CD34+ cultures pre-incubated for 10 minutes at room temperature with Adenosine diphosphate (ADP) or Arachidonic Acid (AA).

DESCRIPTION OF SPECIFIC EMBODIMENTS OF THE INVENTION

The present invention, in some embodiments thereof, relates to compositions and methods for inducing thrombopoiesis.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Thrombocytopenia refers to a decrease in circulating platelet levels which leads to clinical manifestation typically below 50,000/μL. This condition is commonly associated with defective formation of haemostatic plugs and bleeding, wherein the risk of bleeding is inversely proportional to the platelet count.

Currently available treatments for thrombocytopenia and related conditions include, for example, corticosteroids, IVIG, splenectomy, injections of Thrombopoietin (TPO) and TPO mimetics, and whole blood or platelet transfusion, methods which are either palliative and non-specific, or drastic and expensive. Additionally, continuous platelet transfusions can cause immunologic platelet destruction.

Livin, a member in the IAP family of proteins, was previously shown to be expressed in platelets, and bone marrow (BM) megakaryocytes (MKs) and to induce differentiation of LAMA-84 erythroleukemic cell line to platelets.

Whilst reducing the present invention to practice, the present inventors have now uncovered that Livin and its truncated form tLivin are capable of inducing differentiation of hematopoietic stem or progenitor cells towards functional platelets. Without being bound to theory it is suggested that Livin uses both its anti-apoptotic and pro-apoptotic functions to play a differential regulatory role in MKs development and platelet production.

Specifically, the present inventors have uncovered that the anti-apoptotic Livin plays a role in thrombopoiesis, possibly by reducing early caspase-3 activity and inhibiting MKs apoptosis at its early stage of differentiation. At terminal stages of MK maturation, Livin cleavage (resulting in pro-apoptotic tLivin) allows apoptosis to occur simultaneously with platelet production. Most importantly, the present inventors have uncovered that the pro-apoptotic function of tLivin is essential for production of functional Platelets from MKs.

Taken together, according to this invention both Livin and tLivin can be used to induce formation of platelets in-vivo, in-vitro or ex-vivo.

As is illustrated hereinunder and in the examples section, which follows the present inventors show that Livin is expressed in human blood platelets and in BM MKs (Example 1, FIGS. 1A-1D). LAMA-84 cells treated with PMA differentiate to polyploid CD41+ MKs that express Livin and produce functional platelet like particles (PLPs) (Example 2, FIGS. 2-3). As is shown in FIGS. 4A-4D using over-expression of Livin (by transfection), Livin is cleaved at the terminal stage of MKs differentiation. The inventors further demonstrate that caspase-3 activation is increased at the final stage of differentiation when wild-type Livin is over expressed in comparison to control and to $Livin_{RING}$ (Livin mutant lacking the pro-apoptotic function) over-expression. Moreover, $Livin_{RING}$ overexpression resulted in formation of non-functional PLPs. Thus, the pro-apoptotic function of tLivin is essential for both Caspase-3 activation and formation of functional platelets (Example 3, FIGS. 4A-4D). Additionally, knock down of Livin reduces the ability of LAMA-84 originated MKs to produce functional platelets (Example 3, FIG. 7A-7C).

The inventors further demonstrate in FIGS. 5-6 and FIGS. 7D-7E that over expression of wild-type Livin in CD34+ cells in combination with stem cell factor (SCF) and TPO results in differentiation to polyploid CD41+ MKs expressing both Livin and tLivin that produce functional PLPs. Down regulation of Livin decreased significantly MK differentiation and platelets functionality. The pro-apoptotic effect of tLivin did not seem to affect the extent of platelets production, but affected their functionality. Thus, the pro-apoptoic function of tLivin is essential for formation of functional platelets (Example 4, FIGS. 5-6 and FIGS. 7D-7E).

Consequently, the present teachings suggest that Livin and functional portions thereof can be used to induce platelets production in-vivo, in-vitro or ex-vivo.

Thus, according to a first aspect of the present invention, there is provided a method of inducing thrombopoiesis, the method comprising contacting stem cells with a differentiation potential towards platelets or hematopoietic progenitor cells derived therefrom with Livin, thereby inducing thrombopoiesis.

According to another aspect of the invention there is provided a method of inducing thrombopoiesis, the method comprising contacting cells with a differentiation potential towards platelets with tLivin, thereby inducing thrombopoiesis.

As used herein, the term "thrombopoiesis" refers to the process of functional platelets generation. The process is initiated by the differentiation of a cell having differentiation potential towards platelets to megakaryocytes (MKs) and continues with the differentiation of the MKs towards functional platelets. Thrombopoiesis can occur under physiological in-vivo conditions but also in in-vitro or ex-vivo settings. The in-vitro counterpart to thrombopoiesis is termed the "pro-platelet" process and results in production of platelet-like particles (PLPs).

As used herein, the term "platelets" refers to both platelets and PLPs.

As used herein, "inducing thrombopoiesis" refers to an increase of at least 5% in proliferation, differentiation and/or production of MKs and/or platelets. According to a specific embodiment, the increase is in at least 10%, 20%, 30% or even higher say, 50%, 70%, 90% or more than 100%.

As mentioned herein, "functional platelets" refers to platelets that contribute to the maintenance of hemostasis by formation of a hemostatic plug, development of coagulation and consolidation of the hemostatic plug. Platelets function can be assessed in multiple ways, including but not limited to adhesion, aggregation, flow cytometry to assess the state of platelet activation, and in-vivo bleeding time.

The bleeding time test assesses in-vivo platelet function. The bleeding time is defined as the time it takes for a standardized skin wound to stop bleeding. It is based on the fact that when vessel injury is induced by a standardized cutting implement, platelets adhere, aggregate, and form a hemostatic platelet plug. The bleeding time measures the ability of platelets to arrest bleeding and, therefore, is a measure of both platelet number and function. Normal bleeding time is less than 10 min. Platelet aggregation test assays the ability of platelets to adhere to one another in response to stimulation by an exogenous substance (agonist) in-vitro. Examples for possible agonists are adenosine diphosphate (ADP), epinephrine, arachidonic acid (AA), collagen, and Ristocetin. Upon the addition of an agonist, the platelets change shape from a disc shape to a more rounded form with pseudopods, resulting in a transient, small decrease in light transmission that is followed by a large increase as the platelets aggregate. The rate and extent of the increase in light transmission is measured using a platelet aggregometer, a photo-optical or electrical impedance instrument connected to a chart recorder.

Platelet activation (e.g.; by the above mentioned agonists) results in conformational and surface expression changes and in membrane glycoproteins and proteins. For example, the alpha granule transmembrane protein, P-selectin, appears on the surface of platelets when they are stimulated to secrete their granule contents. Thus, platelet function can be measured by P-selectin expression as evaluated by flow cytometry.

The Cone and Plate(let) Analyzer (CPA) measures platelet adherence and aggregation under conditions of high shear using a cone-and-plate viscometer. This device induces laminar flow with a uniform shear stress over a plate surface covered by a rotating cone. A small volume of a sample (for example citrated whole blood) is applied to the polystyrene plate and is subjected to a defined shear rate for 2 min, followed by staining. Adherent platelets and platelet aggregates are evaluated by an image analyzer that provides a size distribution histogram, the percent of surface coverage, and average size of the stained objects.

As used herein, the phrase "cells having differentiation potential towards platelets" refer to stem cells or progenitor cells, such as hematopoietic progenitor cells which can differentiate to platelets.

Examples of "cells with a differentiation potential towards platelets" include but are not limited to cells selected from the group consisting of stem cells with a differentiation potential towards platelets, CD34+ cells, hematopoietic progenitor cells derived therefrom, and hematopoietic precursor cell lines. An example of a cell line includes but is not limited to LAMA-84, LAMA-87, HEL, AP217, UT-7, or Dami. LAMA-84 is a BCR-ABL positive erythroleukemic cell line established from peripheral blood of a 29-year-old woman with chronic myeloid leukemia (CML) (treated 5 years with busulfan) one month after onset of myeloid-megakaryocytic blast crisis. LAMA-84 cells were described to express megakaryocytic and erythroid markers and to respond to induction of differentiation with various reagents.

According to a specific embodiment, the cell having differentiation potential towards platelets is a stem cell with a differentiation potential towards platelets.

As used herein, the phrase "stem cells" refers to cells which are capable of remaining in an undifferentiated state (e.g., pluripotent or multipotent stem cells) for extended periods of time in culture until induced to differentiate into other cell types having a particular, specialized function (e.g., fully differentiated cells).

According to a specific embodiment, the phrase "stem cells" encompasses embryonic stem cells (ESCs), induced pluripotent stem cells (iPS), adult stem cells and hematopoietic stem cells.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763). According to a specific embodiment, embryonic stem cells are obtained without the destruction of embryos, as further described hereinbelow.

Induced pluripotent stem cells (iPS; embryonic-like stem cells), are cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin) and undergo de-differentiation by genetic manipulation which re-programs the cell to acquire embryonic stem cells characteristics. According to some embodiments of the invention, the induced pluripotent stem cells are formed by inducing the expression of Oct-4, Sox2, Kfl4 and c-Myc in a somatic stem cell. The phrase "adult stem cells" (also called "tissue stem cells" or a stem cell from a somatic tissue) refers to any stem cell derived from a somatic tissue [of either a postnatal or prenatal animal (especially the human)]. The adult stem cell is generally thought to be a multipotent stem cell, capable of differentiation into multiple cell types. Adult stem cells can be derived from any adult, neonatal or fetal tissue such as adipose tissue, skin, kidney, liver, prostate, pancreas, intestine, bone marrow and placenta.

Hematopoietic stem cells, which may also referred to as tissue stem cells (which may be derived from adult or neonate subjects), include stem cells obtained from blood or bone marrow tissue of an individual at any age or from cord blood of a newborn individual. According to a specific embodiment the Hematopoietic stem cells are mobilized to the peripheral blood by agents such as G-CSF with or without chemotherapy.

Placental and cord blood stem cells may also be referred to as "young stem cells".

The embryonic stem cells of some embodiments of the invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used according to some embodiments of the invention. Human ES cells can be purchased from the NIH human embryonic stem cells registry [Hypertext Transfer Protocol://grants (dot) nih (dot) gov/stem_cells/registry/current (dot) htm]. Non-limiting examples of commercially available embryonic stem cell lines are BG01, BG02, BG03, BG04, CY12, CY30, CY92, CY10, TE03, TE32, CHB-4, CHB-5, CHB-6, CHB-8, CHB-9, CHB-10, CHB-11, CHB-12, HUES 1, HUES 2, HUES 3, HUES 4, HUES 5, HUES 6, HUES 7, HUES 8, HUES 9, HUES 10, HUES 11, HUES 12, HUES 13, HUES 14, HUES 15, HUES 16, HUES 17, HUES 18, HUES 19, HUES 20, HUES 21, HUES 22, HUES 23, HUES 24, HUES 25, HUES 26, HUES 27, HUES 28, CyT49, RUES3, WA01, UCSF4, NYUES1, NYUES2, NYUES3, NYUES4, NYUES5, NYUES6, NYUES7, UCLA 1, UCLA 2, UCLA 3, WA077 (H7), WA09 (H9), WA13 (H13), WA14 (H14), HUES 62, HUES 63, HUES 64, CT1, CT2, CT3, CT4, MA135, Eneavour-2, WIBR1, WIBR2, WIBR3, WIBR4, WIBR5, WIBR6, HUES 45, Shef 3, Shef 6, BJNhem19, BJNhem20, SA001, SA001.

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, Mo., USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

Another method for preparing ES cells is described in Chung et al., Cell Stem Cell, Volume 2, Issue 2, 113-117, 7 Feb. 2008. According to this method hESC can be generated from single blastomer biopsied from an embryo using a technique similar to pre-implantation genetic diagnosis (PGD). The biopsied blastomer is first co-cultured with the parental embryo for 12-24 hours and then seeded on a feeder layer and cultured using a modified approach aimed at recreating the ICM niche by preventing trophectoderm differentiation by using medium supplemented with laminin and fibronectin. The embryo is not destroyed in the process. The stem cell lines generated according to this method have the same characteristics as other hESC lines, including expression of the same markers of pluripotency, self-renewing capacity, karyotypic stability and ability to differentiate into derivatives of all three germ layers both in vitro and in vivo.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

Induced pluripotent stem cells (iPS) (embryonic-like stem cells) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripotent Stem Cells from Adult Mouse Liver and Stomach Cells. Science. 2008 Feb. 14. (Epub ahead of print); IH Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear transfer into zygotes if the recipient cells are arrested in mitosis.

Adult tissue stem cells can be isolated using various methods known in the art such as those disclosed by Alison, M. R. [J Pathol. 2003 200(5): 547-50], Cal, J. et al., [Blood Cells Mol Dis. 2003 31(1): 18-27], Collins, A. T. et al., [J Cell Sci. 2001; 114 (Pt 21): 3865-72], Potten, C. S. and Morris, R. J. [Epithelial stem cells in vivo. 1988. J. Cell Sci. Suppl. 10, 45-62], Dominici, M et al., [J. Biol. Regul. Homeost. Agents. 2001, 15: 28-37], Caplan and Haynesworth [U.S. Pat. No. 5,486,359] Jones E. A. et al., [Arthritis Rheum. 2002, 46(12): 3349-60]. Fetal stem cells can be isolated using various methods known in the art such as those disclosed by Eventov-Friedman S, et al., PLoS Med. 2006, 3: e215; Eventov-Friedman S, et al., Proc Natl Acad Sci USA. 2005, 102: 2928-33; Dekel B, et al., 2003, Nat Med. 9: 53-60; and Dekel B, et al., 2002, J. Am. Soc. Nephrol. 13: 977-90. Hematopoietic stem cells can be isolated using various methods known in the arts such as those disclosed by "Handbook of Stem Cells" edit by Robert Lanze, Elsevier Academic Press, 2004, Chapter 54, pp609-614, isolation and characterization of hematopoietic stem cells, by Gerald J Spangrude and William B Stayton.

According to a specific embodiment, the stem cell having differentiation potential towards platelets is a hematopoietic stem cell or a hematopoietic progenitor cell derived therefrom.

According to a specific embodiment, hematopoietic stem cell is a CD34+ cell. As used herein the term "CD34+ cell" refers to a hematopoietic stem cell positive for the CD34 marker that can differentiate to each of the cell types in the blood, i.e; the myeloid (monocyte, macrophage, neutrophil, basophil, eosinophil, erythrocyte, megakaryocyte, dendritic cell) or lymphoid (T cell, B cell, NK cell) lineages.

As used herein, the term "a hematopoietic progenitor cell derived from a stem cell" refers to hematopoietic progenitor cell that can differentiate to platelets, for example but not limited to a myeloid precursor cell or MK.

According to a specific embodiment the megakaryocyte progenitor is CD41+CD34+.

The hematopoietic progenitor cells may be a specific cell line, alternatively may be generated from iPS or embryonic stem cells [see for example Pick M et al. (2007) Stem Cells, 25(9): 2206-14; and Pick M et al. (2013) PLoS One, 8(2): e55530] or alternatively may be isolated from cord blood, peripheral blood or BM samples by means of density gradient centrifugation using for example Ficoll-Paque (can be obtained from GE Healthcare Bio-Science AB) followed by immunomagnetic or immunofluorescent methods (such as Diamond or Microbeads CD34+ isolation kit obtained from Miltenyi Biotech). Purity of the purified fraction can be assessed by flow cytometry for the specified markers (for example CD34). According to a specific embodiment the hematopoietic progenitor cells comprise MKs. The cell can be a primary cell (non-cultured and alternatively or additionally non-immortalized cell) or a cell-line.

As mentioned the cells are contacted with Livin.

As used herein "Livin" also known as baculoviral IAP repeat-containing 7; BIRC7, KIAP, ML-IAP and Livin inhibitor-of-apoptosis, refers to a functional expression product of BIRC7 gene which is a member in the anti-apoptotic IAP family of proteins. A functional expression product of Livin refers to a Livin protein product which is able to induce the production of functional platelets. Assays for testing production of functional platelets are well known in the art and mentioned hereinabove.

Livin contains a single baculovirus IAP repeats (BIR) domain at the N-terminus and a carboxy-terminal RING domain[29-31]. The BIR domain was shown to play a role in the anti-apoptotic function of IAPs[26,27]. Human Livin encodes two highly similar splicing variants, termed Livin α and β that differ only in 18 amino acids located between the BIR and the RING domains, which are present in the α but not in the β isoform. Following apoptotic stimuli, both Livin isoforms α and β undergo a specific proteolytic cleavage that trims the 52 amino acids at the N-terminus of Livin. From each isoform a C-terminal Livin truncated protein is thus produced, of approximately 30 kDa (also termed "p30" or tLivin α) and 28 kDa (also termed "p28" or tLivin β), respectively, containing the full BIR and RING domains (Ashhab, Y. et al. FEBS letters, 495: 56-60 (2001)). These truncated forms of Livin are collectively referred to as tLivin. tLivin is not only devoid of Livin anti-apoptotic activity but also acquires a pro-apoptotic effect[32,33].

Thus, specific examples of Livin which can be used according to the present teachings include but are not limited to full length Livin, Livin α isoform, Livin β isoform, tLivin, tLivin α, tLivin β, p30-Livin α, and p28-Livin β. According to specific embodiments Livin is Livin α isoform (SEQ ID NO: 1 (NM_139317.2) or SEQ ID NO: 2) or a Livin β isoform (SEQ ID NO: 5 (NM_022161.3) or SEQ ID NO: 6).

According to specific embodiments Livin is tLivin.

According to specific embodiments tLivin can be p30-livin α, SEQ ID NO: 3 or 4 disclosed in U.S. Pat. No. 7,517,949.

According to yet other specific embodiments tLivin can be p28-Livin β, SEQ ID NO: 7 or 8 disclosed in U.S. Pat. No. 7,517,949.

According to one embodiment Livin is human Livin.

The term "Livin" also refers to functional Livin homologues which exhibit the desired activity (i.e., induction of thrombopoiesis). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID NOs: 2, 4, 6, or 8 or 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same (as further described hereinbelow).

Sequence identity or homology can be determined using any protein or nucleic acid sequence alignment algorithm such as Blast, ClustalW, and MUSCLE.

It is suggested that Livin plays a dual role in thrombopoiesis. The anti-apoptotic Livin is involved in the early stage of MK differentiation by reducing caspase-3 activity and inhibiting MKs apoptosis. The pro-apoptotic cleaved Livin (tLivin) is essential for production of functional platelets and PLPs at terminal stages of MK maturation, while allowing apoptosis to occur simultaneously with platelet production.

According to a specific embodiment, contacting with Livin is effected in-vitro.

According to another specific embodiment, contacting is effected in-vivo.

According to another specific embodiment, contacting is effected ex-vivo.

Contacting can be effected with Livin which can be either polynucleotide encoding Livin or Livin-derived polypeptide.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

Exemplary nucleic acid sequences encoding Livin which can be used in accordance with the present teachings include, but are not limited to, SEQ ID NOs: 1, 3, 5, or 7.

To express exogenous Livin in mammalian cells, the polynucleotide sequence encoding Livin is preferably ligated into a nucleic acid construct suitable for mammalian cell expression. Such a nucleic acid construct includes a promoter sequence for directing transcription of the polynucleotide sequence in the cell in a constitutive or inducible manner.

The nucleic acid construct (also referred to herein as an "expression vector") of some embodiments of the invention includes additional sequences which render this expression vector suitable for replication and integration in prokaryotes, eukaryotes, or preferably both (e.g., shuttle vectors). In addition, a typical cloning vector may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

According to a specific embodiment, the promoter utilized by the nucleic acid construct of some embodiments of the invention is active in the specific cell population transformed. Examples of cell type-specific promoters include promoters such as GP11b (also known as CD41, Itga2b) promoter that is specifically expressed in MKs (Denarier, E. et al. (1993) Biochem. Biophys. Res. Commun. 30; 195(3): 1360-4), WASP and CD45 promoters that are specifically expressed in hematopoietic cells (Franco, A. Ballabio, et al. (1998) Blood, 91: 4554-4560, and J F DiMartino, et al. (1994) International Immunology, 6(8):1279-83, respectively), and CD34 promoter that is specifically expressed in hematopoietic stem cells and progenitors (Burn T C et al. (1992) Blood, 80(12):3051-9).

In addition to the elements already described, the expression vector of some embodiments of the invention may contain enhancer elements, Polyadenylation sequences, eukaryotic replicon or other specialized elements.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

Examples for mammalian expression vectors include, but are not limited to pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Other than containing the necessary elements for the transcription and translation of the inserted coding sequence, the expression construct of some embodiments of the invention can also include sequences engineered to enhance stability, production, purification, yield or toxicity of the expressed peptide.

The Livin polynucleotide of some embodiments of the invention can be introduced into cells by any one of a variety of known methods within the art. Such methods can be found generally described in Sambrook et al., [Molecular Cloning: A Laboratory Manual, Cold Springs Harbor Laboratory, New York (1989, 1992)]; Ausubel et al., [Current Protocols in Molecular Biology, John Wiley and Sons, Baltimore, Md. (1989)]; Chang et al., [Somatic Gene Therapy, CRC Press, Ann Arbor, Mich. (1995)]; Vega et al., [Gene Targeting, CRC Press, Ann Arbor Mich. (1995)]; Vectors [A Survey of Molecular Cloning Vectors and Their Uses, Butterworths, Boston Mass. (1988)] and Gilboa et al. [Biotechniques 4 (6): 504-512 (1986)] and include, for example, stable or transient transfection, electroporation and infection with recombinant viral vectors.

According to a specific embodiment, the Livin polynucleotide is expressed from a viral vector in which case the cells are infected with the virus, as further described hereinbelow. Examples for viral vector include, but are not limited to pWZL-blast which is available, for example, from Addgene.

Alternatively or additionally, Livin is a Livin polypeptide. The term "polypeptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein.

Further details in this respect are provided hereinunder.

Peptide bonds (—CO—NH—) within the peptide may be substituted, for example, by N-methylated amide bonds (—N(CH3)-CO—), ester bonds (—C(=O)—O—), ketomethylene bonds (—CO—CH2-), sulfinylmethylene bonds (—S(=O)—CH2-), α-aza bonds (—NH—N(R)—CO—), wherein R is any alkyl (e.g., methyl), amine bonds (—CH2-NH—), sulfide bonds (—CH2-S—), ethylene bonds (—CH2-CH2-), hydroxyethylene bonds (—CH(OH)—CH2-), thioamide bonds (—CS—NH—), olefinic double bonds (—CH=CH—), fluorinated olefinic double bonds (—CF=CH—), retro amide bonds (—NH—CO—), peptide derivatives (—N(R)—CH2-CO—), wherein R is the "normal" side chain, naturally present on the carbon atom.

These modifications can occur at any of the bonds along the polypeptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The polypeptides of some embodiments of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (e.g., synthetic, Table 2) which can be used with the present invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |

TABLE 1-continued

| Amino Acid | Three-Letter Abbreviation | One-letter Symbol |
|---|---|---|
| Histidine | His | H |
| Isoleucine | Iie | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-Carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-Carboxylate | Norb | L-N-methylglutamine | Nmgln |
|  |  | L-N-methylglutamic acid | Nmglu |
| Cyclohexylalanine | Chexa | L-N-methylhistidine | Nmhis |
| Cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |

TABLE 2-continued

| Non-conventional amino acid | Code | Non-conventional amino acid | Code |
|---|---|---|---|
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

Since the present polypeptides are preferably utilized in therapeutics which require the peptides to be in soluble form, the polypeptides of some embodiments of the invention preferably include one or more non-natural or natural polar amino acids, including but not limited to serine and threonine which are capable of increasing peptide solubility due to their hydroxyl-containing side chain.

The Livin polypeptides of some embodiments of the invention may be synthesized by any techniques known to those skilled in the art of peptide synthesis, for example but not limited to recombinant DNA techniques or solid phase peptide synthesis.

According to some embodiments, Livin is provided in a formulation suitable for cell penetration that enhances intracellular delivery of Livin.

Naked DNA, cell penetrating peptide or Viral and non-viral vectors (e.g. but not limited to liposomes, nanoparticles, mammalian vectors and the like) may be utilized as delivery vehicles in delivery of Livin polynucleotide or Livin polypeptide as is known in the art. According to specific embodiments of the invention, the delivery system used is biocompatible and nontoxic. Following are exemplary embodiments suitable for enhancing penetration of Livin to cells.

According to one exemplary embodiment, naked DNA [e.g., naked plasmid DNA (pDNA)] is non-viral vector which can be produced in bacteria and manipulated using standard recombinant DNA techniques. It does not induce antibody response against itself (i.e., no anti-DNA antibodies generated) and enables long-term gene expression even without chromosome integration. Livin Naked DNA can be introduced by numerous means, for example but not limited to, intravascular and electroporation techniques [Wolff J A, Budker V, 2005, Adv. Genet. 54: 3-20], or by jet injection [Walther W, et al., 2004, Mol. Biotechnol. 28: 121-8].

According to another exemplary embodiment mammalian vectors are used, as further described hereinabove.

According to another exemplary embodiment viral vectors are used. Viral vectors offer several advantages including higher efficiency of transformation, and targeting to, and propagation in, specific cell types. Viral vectors can also be modified with specific receptors or ligands to alter target specificity through specific cell receptors. Moreover, platelets do not have a nucleus, therefore according to specific embodiments of this invention, induction of thrombopoiesis using viral vectors (e.g. Livin cDNA retroviral constructs) in-vitro results in viral free platelets formation that can be safely administered to said subject.

Retroviral vectors represent one class of vectors suitable for use with some embodiments of the invention. Protocols for producing recombinant retroviruses and for infecting cells in-vitro or in-vivo with such viruses can be found in, for example, Ausubel et al., [eds, Current Protocols in Molecular Biology, Greene Publishing Associates, (1989)]. Other suitable expression vectors may be an adenovirus, a lentivirus, a Herpes simplex I virus or adeno-associated virus (AAV).

Features that limit expression to particular cell types can also be included. Such features include, for example, promoter and regulatory elements that are specific for the desired cell type.

According to another exemplary embodiment a Livin encoding polynucleotide or a Livin polypeptide may be incorporated into a particulated delivery vehicle, e.g., a liposome, or a nano- or microparticle. For example, a Livin cDNA may be encapsulated in or attached to a delivery vehicle by any of the known methods in the art [Liposome Technology, Vol. II, Incorporation of Drugs, Proteins, and Genetic Material, CRC Press; Monkkonen, J. et al., 1994, J. Drug Target, 2:299-308; Monkkonen, J. et al., 1993, Calcif. Tissue Int., 53:139-145; Lasic D D., Liposomes Technology Inc., Elsevier, 1993, 63-105. (chapter 3); Winterhalter M, Lasic D D, Chem Phys Lipids, 1993 September; 64(1-3): 35-43].

Liposomes include any synthetic (i.e., not naturally occurring) structure composed of lipid bilayers, which enclose a volume. Liposomes include emulsions, foams, micelles, insoluble monolayers, liquid crystals, phospholipid dispersions, lamellar layers and the like. Liposomes can be of different sizes, may contain a low or a high pH and may be of different charge.

Cell-Penetrating Peptides (CPPs) are short peptides (≤40 amino acids), with the ability to gain access to the interior of almost any cell. They are highly cationic and usually rich in arginine and lysine amino acids. They have the exceptional property of carrying into the cells a wide variety of covalently and noncovalently conjugated cargoes such as proteins, oligonucleotides, and even 200 nm liposomes. Therefore, according to additional exemplary embodiment CPPs can be used to transport Livin polynucleotide or polypeptide to the interior of cells.

TAT (transcription activator from HIV-1), pAntp (also named penetratin, *Drosophila* antennapedia homeodomain transcription factor) and VP22 (from Herpes Simplex virus) are examples of CPPs that can enter cells in a non-toxic and efficient manner and may be suitable for use with some embodiments of the invention. Protocols for producing CPPs-cargos conjugates and for infecting cells with such conjugates can be found, for example L Theodore et al. [The Journal of Neuroscience, (1995) 15(11): 7158-7167], Fawell S, et al. [Proc Natl Acad Sci USA, (1994) 91:664-668], and Jing Bian et al. [Circulation Research. (2007) 100: 1626-1633].

The expression level and/or activity level of the Livin expressed in the cells of some embodiments of the invention can be determined using methods known in the arts, e.g but not limited to Northern blot analysis, PCR analysis, Western blot analysis, Immunohistochemistry, and Fluorescence activated cell sorting (FACS).

As used herein, "expressing" or "expression" refers to gene expression at the RNA and/or protein level.

As mentioned, according to specific embodiments contacting the cells with Livin is effected ex-vivo or in-vitro. Thus, according to specific embodiments, the cells with a differentiation potential towards platelets (e.g., stem cells, CD34+ cells or hematopoietic progenitor cells) are comprised in a biological sample. These stem cells, CD34+ cells or Hematopoietic progenitor cells can be isolated using various methods known in the arts as further described hereinabove.

According to yet specific embodiment the biological sample is selected from the group consisting cord blood, peripheral blood (PB), peripheral blood mononuclear cells (PBMCs) and bone marrow (BM).

According to specific embodiment, the biological sample comprises PBMCs.

According to specific embodiments, the biological sample is an autologous sample, a syngeneic sample, an allogeneic sample or a xenogeneic sample.

According to a specific embodiment, contacting cells with Livin can be performed such that Livin is in direct contact with the cells.

According to some embodiments of the invention, the cells of the subject are incubated with Livin. The conditions used for incubating the cells are selected for a time period/concentration of cells/concentration of Livin/ratio between cells and Livin and the like which enable Livin to induce cellular changes, such as polyploidization, differentiation and/or apoptosis.

According to a specific embodiment, the invention further includes contacting the cells with a platelet production stimulating factor.

As used herein, the term "platelet production stimulating factor" refers to cytokines and growth hormones that have been shown to induce thrombopoiesis.

According to specific embodiments the platelet production stimulating factor is selected from the group consisting of thrombopoietin (TPO), TPO agonist, stem cell factor (SCF) and Phorbol myristate acetate (PMA).

Thrombopoietin (TPO), which is available, for example, from R&D Systems (e.g., Cat No. 288-TP), is the primary physiological growth factor necessary for thrombopoiesis and also plays a central role in the survival and proliferation of hematopoietic stem cells (HSC). TPO affects nearly all aspects of platelet production, from HSC self-renewal and expansion, through stimulation of MK progenitor cell proliferation, to supporting their maturation into platelet-producing cells. Its activity is orchestrated via binding to the MPL receptor, which initiates activation cascades of several signal transduction pathways.

A TPO agonist (or TPO receptor agonist), as used herein, refers to a molecule having a pharmacological activity characteristic of TPO and substantially similar to that of TPO. For example, such molecules may be TPO analogs or mimetics, or other molecules (such as proteins, peptides, antibodies and small molecules) that bind to the c-mpl (TpoR) receptor, the physiological target of thrombopoietin, in an agonistic manner. Common TPO agonists have thrombopoietic activity, e.g. in increasing proliferation and differentiation of MKs. In various specific embodiments, Livin may act in synergistic or additive manners to enhance various aspects of thrombopoiesis or blood platelet levels.

Specific examples of agents that induce or enhance platelets production including commercially available TPO agonists are Romiplostim (AMG-531, marketed under the trade name Nplate), developed by Amgen as a Thrombopoietin receptor-binding peptibody; Eltrombopag (rINN, SB-497115) marketed by GlaxoSmithKline under the trade name Promacta as a TPO receptor agonist; AKR-501 developed by AkaRx as a small molecule thrombopoietin receptor agonist; LGD-4665 developed by Ligand Pharmaceuticals as an oral thrombopoietin mimetic; N-acetylcysteine, suggested by Adherex Technologies as a chemoprotectant for the prevention of bone marrow suppression resulting from certain chemotherapy regimens; peg-TPOmp developed by Johnson & Johnson as a pegylated peptide thrombopoietin receptor agonist; and SB-559448, developed by GlaxoSmithKline and Ligand Pharmaceuticals as an oral non-peptide small molecule thrombopoietin receptor agonist.

Stem Cell Factor (SCF), which is available, for example, from R&D Systems (e.g., Cat. No. 255-SC), is a cytokine that binds to the c-Kit receptor. This cytokine has been shown to play important complex roles in hematopoiesis, spermatogenesis, and melanogenesis. As used herein, SCF has been shown to increase the survival of MK progenitors in-vitro and to affect developmentally early aspects of MK growth [Virginia C. Broudy (1997) Blood 90(4): 1345-1364; Kenneth Kaushansky (2009) Hematology, 147-152].

Phorbol myristate acetate (PMA), which is available, for example, from Sigma-Aldrich (e.g., Cat. No. P8139), is a diester of phorbol that activate the signal transduction enzyme protein kinase C (PKC). PMA has been shown to induce differentiation of immature HSC, activate T cells, induce monocyte/macrophage differentiation of promyelocytic leukaemia cell lines, and stimulate fibrinogen binding and phosphorylation of the focaladhesion kinase in platelets. Additionally, PMA has been shown to induce MK transformation in few cell lines, for example HEL, LAMA-84 and AP217 [Gauthami Jalagadugula et al. (2010) Blood. 116 (26): 6037-6045; Annie MOLLA et al. (1995) Biochem. J. 309: 491-497].

Other cytokines that may stimulate platelet production include e.g. IL-1, IL-3, IL-6 and GM-CSF.

Appropriate doses and administration schemes of such co-administered drugs e.g. TPO agonists are available to those of skill in the art.

During the culturing step the cultured cells are further monitored for their cellular changes and differentiation state. Cell differentiation can be determined upon examination of morphology, polyploidy and cell markers which are known to be indicative of MK differentiation, for example expression of CD41 marker. Cell specific markers can be detected using immunological techniques well known in the art (Thomson J A et al., (1998) Science 282: 1145-7). Examples include, but are not limited to, flow cytometry (FACS) for membrane-bound markers and immune-histochemistry for extracellular and intracellular markers.

It will be appreciated that MKs and platelets are of a distinct morphology, which is clearly distinguishable from undifferentiated stem cells, CD34+ cells, hematopoietic progenitor cells derived therefrom or LAMA-84 by the skilled in the art.

Thus, according to an aspect of the invention there is provided an isolated population of cells generated by contacting cells with a differentiation potential towards platelets with Livin in-vitro or ex-vivo.

As used herein the term "isolated" refers to at least partially separated from the natural environment e.g., the human body or a blood sample.

The cells of the present teachings can be undifferentiated cells which comprise the exogenous Livin but haven't gone differentiation to MKs and/or functional platelets.

According to another embodiment, the cells are those which have undergone differentiation such as MKs (e.g., which comprise the nucleic acid sequence encoding Livin) or functional platelets.

According to a specific embodiment of the invention the isolated population of cells is positive for one or more MKs and/or platelets specific marker. Positive is also abbreviated by (+). Positive for a marker means that at least about 70%, 80%, 85%, 90%, 95%, or 100% of the cells in the population present detectable levels of the marker (e.g., CD41) assayed by a method known to those of skill in the art, such as flow cytometry.

According to a specific embodiment the CD41+ cells stain negatively to one or more marker e.g., CD71. Negative is also abbreviated by (−). Negative for a marker means that no more than about 5%, 10%, 20%, 25%, or 30% of the cells in the population present detectable levels of the marker (e.g., CD71) assayed by a method known to those of skill in the art such as FACS. Such a marker presentation either of a single cell or an isolated population of cells is also referred to as a signature.

According to a specific embodiment of the invention the isolated population of cells present increase in ploidy as compared to stem cells with a differentiation potential towards platelets or hematopoietic progenitor cells derived therefrom that were not contacted with Livin, as assayed by flow cytometry.

According to other specific embodiment of the invention the isolated population of cells present increase in the number of nuclei per cell as compared to stem cells with a differentiation potential towards platelets or hematopoietic progenitor cells derived therefrom that were not contacted with Livin, as assayed by May Grumwald/Giemsa staining.

Thus, the present compositions comprising e.g., Livin, cells which express the same and cells differentiated therefrom (e.g., MKs and platelets) can be used in clinical settings.

Thus, according to an aspect of the invention there is provided a method of treating thrombocytopenia in a subject in need thereof, the method comprising administering to the subject a therapeutically effective amount of the above mentioned Livin or isolated population of cells, thereby treating thrombocytopenia in the subject.

According to another aspect there is provided a method of inducing thrombopoiesis in a subject in need thereof, the method comprising administering to the subject a therapeutically effective amount of Livin or the isolated cell population as described herein, thereby inducing thrombopoiesis in the subject.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. In a specific embodiment, this term encompasses individuals who are at risk to develop the pathology.

"Thrombocytopenia", as used herein, refers to a relative decrease below the physiological range of circulating platelets in blood of said subject. Typically, a normal platelet count is between 150,000 to 450,000/μL. Thrombocytopenia is typically associated with defective formation of haemostatic plugs and bleeding, wherein the risk of bleeding is inversely proportional to the platelet count. When the platelet count is lower than 50,000/μL, minor bleeding occurs easily and the risk of major bleeding increases, and counts between 20,000 and 50,000/μL predispose to bleeding with trauma, even minor trauma. With counts lower than 20,000/μL, spontaneous bleeding may occur; with counts lower than 5000/μL, severe spontaneous bleeding is more likely, and the severe thrombocytopenia is often referred to as life threatening thrombocytopenia.

Platelet levels may be lowered by the reduction of platelet productivity in BM, or by platelet consumption, promotion of platelet degradation in periphery, or abnormal platelet distribution. For example, thrombocytopenia can be due to antibody mediated platelet destruction or BM failure from e.g. malignant infiltration or chemotherapy.

Diagnosis of the particular condition is typically performed using peripheral blood smears and if necessary bone marrow aspiration; increased splenic sequestration is suggested by splenomegaly.

Thrombocytopenia may be caused by diminished or absent MKs in the BM, e.g. in patients with aplastic anemia or leukemia, in patients receiving myelosuppressive drugs (e.g., chemotherapy), and in some patients with paroxysmal nocturnal hemoglobinuria. Thrombocytopenia may also stem from diminished platelet production despite the presence of MKs in the BM, e.g. in alcohol-induced thrombocytopenia, HIV-associated thrombocytopenia, Myelodysplastic syndromes and vitamin B12 or folate (folic acid) deficiency.

According to specific embodiments, the methods of the invention are useful for elevating the levels of platelets of a subject suffering from or is at a risk of platelet reduction associated with exposure to radiation or chemotherapy.

According to various embodiments, the methods of the invention are effected in subject treated with anti thrombocytopenia therapy.

A used herein, the term "anti thrombocytopenia therapy refers to platelet production stimulating factor (e.g. but not limited to TPO, TPO agonist or SCF) or other agents that are used in the treatment of thrombocytopenia as known in the art (e.g. corticosteroids or immunosuppressants that are indicated for the treatment of thrombocytopenia) according to standard protocols.

According to specific embodiments the anti thrombocytopenia therapy is a platelet production stimulating factor.

According to certain other embodiments, the invention further includes co-administering to the subject other cells, such as but not limited to, hematopoietic stem cell transplantation.

The compositions of the present invention can be administered to the subject per se or as a part of a pharmaceutical composition.

According to a specific embodiment the pharmaceutical composition comprises as active ingredients Livin and a platelet production stimulating factor and a pharmaceutically acceptable carrier or diluent.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to any one of Livin, or cells generated according to the present teachings and a platelet production stimulating factor, accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

As mentioned, the isolated population of cells of some embodiments of the invention can be derived from either autologous, syngeneic, allogeneic, or xenogeneic sources. Since non-autologous cells are likely to induce an immune reaction when administered to the human body several approaches have been developed to reduce the likelihood of rejection of non-autologous cells. These include either suppressing the recipient immune system or encapsulating the non-autologous cells in immunoisolating, semipermeable membranes before transplantation.

Optionally, the active ingredients may be administered in concurrent or sequential combination.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, suitable routes of administration may be in local rather than in systemic manner, for example, via injection of the active ingredient directly into a tissue region of a patient.

Pharmaceutical compositions of some embodiments of the invention may be manufactured by processes well known in the art, e.g., by means of conventional mixing, dissolving, granulating, dragee-making, levigating, emulsifying, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen. Formulations described herein may be prepared by any method known or hereafter developed in the art of pharmacology. Techniques for formulation and administration of drugs may be found in "Remington's Pharmaceutical Sciences," Mack Publishing Co., Easton, Pa., latest edition, which is incorporated herein by reference.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (Livin and a platelet production stimulating factor) effective to prevent, alleviate or ameliorate symptoms of a disorder (e.g., thrombocyopenia) or prolong the survival of the subject being treated.

Determination of a therapeutically effective amount is well within the capability of those skilled in the art. For any preparation used in the methods of the invention, the therapeutically effective amount or dose can be estimated initially from in-vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in-vitro, in cell cultures or experimental animals. The data obtained from these in-vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to assure the active ingredient is sufficient to induce or suppress the biological effect (minimal effective concentration, MEC). The MEC will vary for each preparation, but can be estimated from in-vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing one or more of the active ingredients. The pack may, for example, comprise metal or plastic foil, such as a blister pack. The pack or dispenser device may be accompanied by instructions for administration. In line with various embodiments, this pack may be used in-vivo, in-vitro or ex-vivo. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to specific embodiment there is provided an article of manufacture or a kit identified for inducing thrombopoiesis comprising a packaging material packaging Livin and a platelet production stimulating factor.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. For generation of MKs from embryonic stem cells the references are Pick M, Azzola L, Mossman A, Stanley E and Elefanty A (2007). BMP4 and VEGF are required for the generation of hematopoietic cells from human embryonic stem cells. Stem Cells, 25(9), pp 2206-14 and Pick M, Azzola L, Stanley E and Elefanty A (2013). Generation of Megakaryocytic Progenitors from Human Embryonic Stem Cells in a Feeder- and Serum-Free Medium. PLoS One, 8(2): e55530. Other general references are provided throughout this document. The procedures therein are believed to be well known in the art and are provided for the convenience of the reader. All the information contained therein is incorporated herein by reference.

Materials and Methods

Cells—

Human BCR-ABL positive erythroleukemia cell line, LAMA-84, was obtained from Hadassah Medical Center, Jerusalem, Israel (Seigneurin D. et al., (1987) Exp Hematol. 15(8): 822-832).

Use of all human cell samples and tissues in this study was approved by the Institutional Review Board of the Helsinki Committee at Hadassah-Hebrew University Medical Center. Cord blood samples were obtained from public sources (BEDOMAICH CHAYI, Jewish cord blood bank, Jerusalem, Israel) and CD34+ cells were separated within 48 hours of collection according to the below procedure. Human platelets were generated from normal blood and cord blood of healthy individuals. Samples were collected in tubes containing acid-citrated-dextrose (ACD) solution (2.5% trisodium citrate, 1.5% citric acid and 2%). Platelet-rich plasma (PRP) was obtained by centrifugation at 150×g for 20 minutes at room temperature.

Human bone marrow tissues of hematological patients without bone marrow involvement and patients with immune thrombocytopenic purpura (ITP) were obtained from Hadassah Medical Center pathology archives.

Separation of CD34+ Cells from Cord Blood—

Mononuclear cells (MNCs) were isolated by Ficoll-Paque (GE Healthcare Bio-Science AB) density gradient centrifugation. $CD34^+$ cell enrichment was performed using either the Diamond or Microbeads CD34 isolation kit (Miltenyi Biotech) according to the manufacturer's protocol. Purity of the $CD34^+$ fraction was assessed by flow cytometry and in all cases was higher than 85%.

Induction of Megakaryocyte Differentiation—

LAMA-84 cells were maintained in RPMI1640 containing 10% fetal calf serum, 100 U/ml penicillin, 100 µg/ml streptomycin and 2 mM glutamine. To induce differentiation, the cell culture was supplemented with 0.6-5 ng/ml PMA or 50 µM Hemin and cells were harvested and analyzed 1-5 days following treatment.

Human CD34+ cells were cultured in Iscove's medium (IMDM) ($1\times10^5$ cells/well) and induced to differentiate into MKs in the presence of 10 ng/ml stem cell factor (SCF) and 50 ng/ml thrombopoietin (TPO), freshly supplemented every 3 days. Cells were harvested and analyzed on day 14.

Retroviral vectors and infections—Retroviral constructs were generated by sub-cloning Livin β and Livin $β_{RING}$ (Livin β mutant lacking pro-apoptotic activity, abbreviated herein as RING) cDNA (SEQ ID NO: 5 (NM_022161.3) and SEQ ID NO: 9, respectively into the pWZL IRES-blasticidin vector as described previously[34]. Briefly, the pIRES-Livin β or pIRES-Livin $β_{RING}$ plasmids were digested with EcoR1 and Xho1 and Livin β and Livin $β_{RING}$ cDNA were sub-cloned into the EcoRI-BglII sites of the pWZL IRES-blasticidin vector.

The primers used to generate Livin β were:

```
Forward primer EcoRI-Start,
                                      (SEQ ID NO: 11)
5'-GGGGAATTCTGGTCAGAGCCAGTGTTC-3;

Reverse primer BamHI-Stop,
                                      (SEQ ID NO: 12)
5'-GGGGGATCCGGAGCCCACTCTGCA-3.
```

The primers used to generate Livin β harboring a RING mutation were:

```
Forward primer EcoRI-start,
                                      (SEQ ID NO: 11)
5'-GGGGAATTCTGGTCAGAGCCAGTGTTC-3.

Reverse primer C274A-Stop
                                      (SEQ ID NO: 13)
5'-GGGGGATCCCTAGGACAGGAAGGTGCGCACGCGGCTGCGGACGGG
GGCTCTGCAGATGGGGGCCAGCTGC-3'.
```

293T cells were infected to produce the virus and supernatant from 48 and 72 hours were infected into both LAMA-84 and CD34+ cells during their differentiation induction phase. In order to over-express Livin both LAMA-84 and CD34+ cells were infected following 1 day of differentiation with pWZL IRES-blasticidin vector expressing wild-type Livin (Livin β), $Livin_{RING}$ (Livin β RING), or empty vector (EV). For down-regulating expression of endogenous Livin, LAMA-84 were transfected by electroporation with pSUPER-Livin-2 (Livin siRNA) or pSUPER-luc (control siRNA) vectors[35] together with pWZL IRES-blasticidin 1 day following differentiation initiation. For down-regulating expression of endogenous Livin in CD34+ cells, cells were infected 1 day after differention with supernatant containing the pSUPER viruses generated by 293T cells.

Analysis of Megakaryocyte Maturation—

To determine the extent of maturation toward MKs $1\times10^6$ cultured cells (LAMA-84 or CD34+ cells) were washed and then labeled with anti-CD41-FITC (GpIIb/IIIa, BD Bioscience, USA), or anti CD71-FITC or combination of anti-CD33-FITC, anti-CD41-PE, and CD34-APC (Beckman Coulter, USA) and analyzed using FACScalibur (Becton Dickinson, USA) for the percentage of $CD41^+$ cells generated.

To determine the amount of ploidy, differentiated LAMA-84 cells were fixed overnight in 75% ethanol at 4° C., labeled with propidium iodide (PI, 50 µg/ml) and analyzed using FACScalibur. Fourteen day differentiated CD34+ were analyzed quantitatively under a microscope following May Grumwald/Giemsa staining for the number of nuclei per cell. Only cells with MK morphology were analyzed.

Isolation of Platelet-Like Particles—

Platelets release into the differentiated cultures was assessed via flow cytometry analysis of the supernatants. Specifically, the culture medium was collected and centrifuged at 150×g for 20 minutes to remove the nucleated cells. The supernatant was then centrifuged at 500×g for 20 minutes to pellet the platelets. Sediments containing platelets and platelet-like particles were resuspended in culture medium in 500 µl aliquots and labeled using anti-CD41-FITC. Cells were analyzed by FACScalibur for CD41 expression and log amplification of forward scatter (FCS) and side scatter (SSC).

Platelet Functionality—

Platelets and Platelet like particles generated from platelets-poor plasma e.g. LAMA-84 differentiated cells were tested for their functionality in aggregation assays using an AGGRAM aggregometer (Helena Laboratories, Beaumont, Tex.) according to the manufacturer's instructions using various agonists: adenosine diphosphate (ADP) (11 µM), arachidonic acid (AA) (1.6 µM), Epinephrine (50 µM), Ristocetin (1.6 mM) (Diamed AG, Morat, Switzerland) or collagen (5 µg/ml) (Helena Laboratories, Beaumont, Tex.).

Since the number of platelets generated from CD34+ cultures was low, platelets derived from these cultures were stimulated for 15 minutes at room temperature (RT) with ADP or AA and activation was assessed via flow cytometry analysis of CD62P (Pselectin)-PE (Beckman Coulter) expression (up regulation of CD62P implies activation).

Western Blot Analysis and Immunoprecipitation—

Whole cell lysates were prepared from $0.25-1\times10^6$ cells using 100 µl lysis buffer [20 mM Tris-HCl, 2 mM EDTA, 6 mM β-Mercaptoethanol, 1% Nonidet P-40 (NP-40), 0.1% SDS and protease inhibitors] at 4° C. for 20 min, with vigorous vortex mixing. Antibodies used were: monoclonal antibody against Livin (clone 88C570) (Imgenex, USA) diluted 1:3000 and Survivin 6E4 monoclonal antibody (Cell Signaling Technology, USA), followed by Envision-HRP (DAKO, Denmark) as a secondary antibody; Polyclonal antibody against XIAP (Cell Signaling Technology, USA), followed by anti-rabbit IgG HRP-linked antibody (Cell Signaling Technology, USA) as a secondary antibody. For immunoprecipitation, equal amounts of protein lysates were pre-cleared with Protein A/G-Agarose (Santa Cruz, USA) together with 1 µg of mouse IgG. Livin was immunoprecipitated from the cleared lysates (using clone 88C570) and the immune complexes were precipitated with Protein A/G-Agarose.

Caspase-3 Activity—

Extracts from $1\times10^6$ cells were prepared by the freeze-thaw method assayed for caspase-3 activity using CaspACE™ Assay System, Colorimetric (Promega, USA), according to manufacturer's instructions.

Immunohistochemistry—

Five µm-thick tissue sections of formalin-fixed paraffin-embedded BM aspiration samples were de-paraffinized and endogenous peroxidase was quenched with 3.3% hydrogen peroxide for 10 min at room temperature. Sections were blocked with 3% goat serum in 50 mM Tris, pH 7.4, for 20 min. The slides were then incubated with 1:100 dilution of 3F9 monoclonal antibody against Livin[36] in 50 mM Tris, pH 7.4, and 3% goat serum overnight, washed, and incubated with goat anti-mouse Ig horseradish peroxidase-conjugated antibody (DAKO, Denmark) for 30 min. The slides were developed with DAB as the chromogen, placed in an enhancing solution (Zymed Laboratories, South San Francisco, Calif.) for 5 min, and counterstained with hematoxylin.

Example 1

Livin is Endogenously Expressed in Megakaryocytes and Platelets

Livin expression in mature bone marrow (BM) megakaryocytes (MKs) was examined via immunohistochemical assay using purified monoclonal anti-Livin antibody (3F9). The mature BM MKs, which were unequivocally recognizable by their morphologic criteria, namely giant size cells with polylobulation of the cell nucleus, were positively stained with anti-Livin (FIG. 1A (control) and FIGS. 1B-1C).

Livin expression in human blood platelets was further substantiated via immunoprecipitation followed by western blot analysis of Livin using mouse monoclonal anti-human Livin antibody (clone 88C570) followed by Envision-HRP as a secondary antibody. The anti-Livin antibody (clone 88C570) has been shown to recognize both Livin α (~39 kDa) and Livin β (~37 kDa) isoforms (Nachmias et al, (2003) Cancer Res. 1; 63(19):6340-9). The results demonstrated the presence of both Livin α and β protein in healthy donors' platelets (FIG. 1D).

Thus, present inventors have discovered that Livin was expressed in human blood platelets obtained from healthy donors and in BM MKs of both hematological patients without bone marrow involvement and of patients with various hematological diseases (such as immune thrombocytopenic purpura (ITP, FIG. 1C), and MDS, Hodgkin's lymphoma, essential thrombocythemia and polycythemia vera of patients (data not shown).

Example 2

PMA Treatment of LAMA-84 Cells Serves as a Useful Model for Megakaryocytic Activation and Differentiation In-Vitro PMA Treatment of LAMA-84 Cells Results in Megakaryocytic Endoreplecation and Differentiation Human primary MKs are difficult to isolate due to their low numbers in human samples and thus the present inventors studied the various stages of MK development, differentiation and maturation in a CML-derived BCR-ABL positive erythroleukemic cell line—LAMA-84. The LAMA-84 cell line can undergo differentiation towards both the megakaryocytic and erythroid lineages, depending on the applied stimulus[37-39]: Phorbol myristate acetate (PMA) stimulates megakaryocytic differentiation whereas Hemin induces erythroid differentiation.

LAMA-84 cell differentiation following PMA treatment was studied via morphological staining of the cells with May Grunwald/Giemsa and via flow cytometry analysis of CD41 (MK marker) and CD71 (erythroid marker) expression. Moreover, ploidy, a marker of MK differentiation, was also determined by flow cytometry using propidium iodide (PI). A range of PMA concentrations was tested and differentiation was obtained at 0.6-10 ng/ml PMA.

The Morphological staining of the differentiated LAMA-84 cells with May Grunwald/Giemsa revealed a marked increase in cell size and extensive multinuclearity after PMA induction and pro-platelet formation (FIG. 2A). Flow cytometry analysis of PI implied the untreated LAMA-84 cells were predominantly diploid (FIG. 2B) but after 4 days of exposure to 5 ng/ml PMA, LAMA-84 cells underwent polyploidization (8N, 16N and 32N) and full differentiation (FIG. 2A and FIG. 2B).

Flow cytometry analysis of the CD41 and CD71 markers indicated that PMA induced differentiation of LAMA-84 cells towards the MK lineage (while Hemin served as a negative control for induction of differentiation towards erythroid development). The results clearly show that in the absence of PMA stimulation, most LAMA-84 cells were CD71+ and CD41−. However, following 4 days of incubation with 5 ng/ml or 10 ng/ml PMA, the cells acquired high levels of CD41 expression (for example an increase from 8.8%±5.6% to 81.9%±10%, p=0.000012 in the presence of 5 ng/ml PMA) (FIGS. 2C-2D). As a negative control, treatment of the LAMA-84 cells with Hemin to induce differentiation towards the erythroid lineage did not increase CD41 expression levels (FIG. 2D).

PMA Treatment of LAMA-84 Cells Results in Expression of Livin

The expression of anti-apoptotic proteins of the Apoptosis Protein Livin family (IAPs) during the differentiation of LAMA-84 cells towards MKs was analyzed by Western blot analysis. The expression of Livin was not detected in untreated LAMA-84 cells, but was up-regulated during PMA-induced differentiation towards the MK lineage (FIG. 2E). Note that in contrast to Livin, the level of Survivin decreased when cells were treated with PMA (FIG. 2E). Additionally, upon differentiation of LAMA-84 cells into MKs, a dose dependent significant decrease in the level of the full length form of XIAP was observed which was accompanied by the appearance of the cleaved 30 kDa fragment of XIAP that has a reduced ability to inhibit caspases[40] (FIG. 2E). As a negative control, treatment of the LAMA-84 cells with Hemin to induce differentiation towards the erythroid lineage did not regulate the levels of the anti-apoptotic proteins of the IAP family tested (FIG. 2E).

PMA Treatment of LAMA-84 Cells Produces Functional Platelets

Morphological examination of the LAMA-84 PMA treated cultures revealed pro-platelet formation. This suggested that PMA not only induced the cells to differentiate towards MKs and increased endoreplication but also induced terminal differentiation of the MKs into platelet like particles (PLP) (FIG. 3A).

To verify this, flow cytometry analysis was performed to determine the presence of CD41+ platelets released into the media. For calibration purposes, normal platelets from peripheral blood were used to establish the forward and side scatter gate analysis and a subsequent CD41+ gate for normal human platelets (FIGS. 3B-3C). The results confirmed that the majority of blood-derived platelets expressed CD41 (FIG. 3C). Untreated LAMA-84 cells spontaneously released PLPs into the culture medium (FIG. 3D) but only a minor proportion of them expressed CD41 (6.5%±2.2%) (FIG. 3E). However, following incubation with PMA the percentage of CD41+ PLPs released to the LAMA-84 culture medium increased significantly (24.3%±3.6%) (FIGS. 3F-3G).

Finally, an aggregation functional test was performed with the use of various agonists including Epinephrine, collagen, ADP and Ristocetin on the PMA treated LAMA-84 culture-derived PLPs. As expected, positive control normal platelets aggregated in response to all agonists (FIG. 3H). Surprisingly, the LAMA-84 derived PLPs also aggregated in response to various agonists including Epinephrine, collagen, ADP (but not Ristocestin) (FIG. 3I). Most importantly, to the best of our knowledge, this is the first demonstration for a leukemia cell line that release particles that function as normal platelets. Thus, the results verify the LAMA-84 derived particles were capable of activation and aggregation thus proving their functionality.

Taken together, the above results show that PMA-induced LAMA-84 cells differentiation was accompanied by changes in cell morphology, polyploidization, acquisition of specific MK marker (CD41), and upregulation of Livin protein expression. Upon differentiation, LAMA-84 cells formed pro-platelets and produced functional PLPs capable of aggregation and thus function as normal platelets.

Example 3

The Role of Livin in Thrombopoiesis, Using the PMA Treated LAMA-84 Cells In-Vitro Model Livin is cleaved during LAMA-84 differentiation into MK The present inventors and others have shown previously that Livin[32] and XIAP[40] are specifically cleaved by effector caspases during apoptosis induced by various stimuli. The caspase-mediated cleaved truncated form of Livin, tLivin, is paradoxically a pro-apoptotic protein[32]. Cleavage of XIAP produces a fragment with a reduced ability to inhibit caspases[40].

To address the mechanism of action of Livin in MKs differentiation, LAMA-84 cells were stably transfected to over-express Livin and the expression and effects of Livin protein during MKs differentiation were tested by means of Western blot analysis, caspase-3 activity, CD41 expression evaluated by flow cytometry and platelets functionality evaluated by aggregation assay (FIGS. 4A-4D). Specifically, control LAMA-84 cells (EV, empty vector) and LAMA-84 cells stably over expressing wild-type Livin or Livin mutant lacking pro-apoptotic activity ($Livin_{RING}$) were treated with PMA for 5 Days. Cells were harvested at 12, 24, 48 and 96 hours for evaluation.

The Western blot analysis demonstrated that XIAP was cleaved and down-regulated early in differentiation of LAMA-84 cells stably transfected to over-express wild-type Livin (48 h, FIG. 4A). In contrast, Livin underwent cleavage only at the terminal stage of differentiation (96 h, FIG. 4A).

Measuring caspase-3 enzyme activity at day 4 showed that over-expression of wild-type Livin induced caspase-3 activation in LAMA-84 cells (diagonal lines, FIG. 4B). To investigate whether the pro-apoptotic tLivin is responsible for the caspase-3 activation during LAMA-84 MK differentiation a Livin protein mutant, with a point mutation in the RING domain ($Livin_{RING}$) was used. tLivin requires an intact RING domain for its pro-apoptotic function[33,34]. The results indicated that Caspase-3 activity in LAMA-84 cells containing Livin$_{RING}$ was significantly reduced compared to those containing wild-type Livin (FIG. 4B).

Flow cytometry analysis using the CD41 marker showed that LAMA-84 cells that over-expressed the wild-type Livin or Livin$_{RING}$ produced more PLPs as compared with control cells ($p<0.035$ and $p=5.0E-05$, respectively) (FIG. 4C).

Interestingly, over-expression of the Livin$_{RING}$ mutant that lacks the pro-apoptotic activity of tLivin, produce more CD41+ PLPs compared to wild type Livin ($p<0.31$).

However, over-expression of the mutant form Livin RING showed a reduced ability of MKs to produce functional PLPs, measured by platelet aggregation, using an AGGRAM aggregometer ($p=0.01$) (FIG. 4D).

Knock-Down of Livin Reduces the Ability of LAMA-84 Originated MK to Produce Functional Platelets Short interference RNA (siRNA) was used to knock down the expression of endogenous Livin in LAMA-84 cells using a construct containing Livin siRNA (pSUPER-Livin-2) which was previously characterized as a specific and efficient inhibitor of Livin expression[35].

First, Western blot analyses of LAMA-84 cells that were transfected with Livin siRNA were performed 4 days post treatment with PMA. Indeed, Livin protein levels were significantly reduced by pSUPER-Livin-2, in comparison with control transfections (pSUPER-luc) (FIG. 7A). Subsequently, the LAMA-84 cells that were transfected with Livin siRNA produced significantly less PLPs during MK differentiation as compared to control cells ($p=0.0095$) (FIG. 7B). The extent of PLPs aggregation in response to ADP or collagen was similar in the control and pSUPER-Livin-2 transfected cells. However, PLPs produced from LAMA-84 cells that were down-regulated for Livin had a reduced ability to aggregate in response to epinephrine ($p=0.0087$) or arachidonic acid ($p=0.00016$) (FIG. 7C).

Taken together, the above results show that the anti-apoptotic Livin plays a role in thrombopoiesis, possibly by reducing early caspase-3 activity and inhibiting MKs apoptosis at its early stage of differentiation. At terminal stages of MK maturation, Livin cleavage (resulting in pro-apoptotic tLivin) allows apoptosis to occur simultaneously with platelet production.

Example 4

Over Expression of Livin in Human CD34+ Cells as a Model to Increase Megakaryocytic Activation and Differentiation In-Vitro Over Expression of Livin in CD34+ Cells Results in Increased Megakaryocytic Endoreplecation and Differentiation To investigate the effect of Livin on primary MK progenitors, human CD34+ cells isolated from cord blood samples, were transduced with Livin, Livin$_{RING}$ or control empty vector and grown for 14 days under MK differentiating conditions with the addition of stem cell factor (SCF) and thrombopoeitin (TPO)[41]. At the terminal stages of primary MKs maturation CD34+ cell cultures were examined morphologically, analyzed for CD41 expression and polyploidy via flow cytometry, and Livin expression and cleavage via Western Blot.

Morphological examination at day 14 showed a marked increase in the CD34+ cell size and the cells seemed to undergo polyploidization (FIG. 5A). The percentage of cells stained for MK marker, CD41 (FIG. 5B), increased in the Livin over-expressing CD34+ cells compared to control cells containing empty vector ($3.7\pm1$ fold, $p=0.029$) (FIG. 5C). The differentiated CD41+ cells at day 14 were also positive for CD45 (data not shown) and presented differential expression of CD33 ($7.4\pm6.9\%$ in control cells, $22.6\pm39.8\%$ in cells over expressing Livin and $12.1\pm14\%$, in cells over-expressing Livin$_{RING}$, n=9) (data not shown). In addition, a significant increase in multi-nucleated MKs ($\geq4$ nuclei) was detected in CD34+ differentiation cultures over-expressing Livin in comparison to MKs that were over-expressing Livin$_{RING}$ or empty vector ($p=0.01$ and $0.02$, respectively, FIG. 5D). The presence of multi-nucleated cells in the cytospin preparation is indicative of the presence of polyploidy MKs.

Interestingly, there was no difference in platelet production between primary MKs that were over-expressing Livin RING compared to empty vector and CD34+ cells differentiated with TPO and SCF factor alone (FIG. 5D).

Assessing the presence of Livin and its cleaved protein, tLivin, at the terminal stages of primary MK progenitors maturation (day 14) showed robust levels in the CD34+ cultures containing the over-expressed Livin protein in comparison to naïve CD34+ cultures and CD34+ cultures infected with control empty vector (FIG. 5E).

Over Expression of Livin in Human CD34+ Cells Results in Functional Platelets Production The following experiments evaluated whether functional platelets were generated from the human CD34+ cell cultures that were transduced with Livin, Livin$_{RING}$ or control empty vector and grown for 14 days under MK differentiating conditions with the addition of SCF and TPO. Platelets released into the media were characterized for CD41 expression and functionality by CD62P up regulation via flow cytometry.

Normal platelets from cord blood were used to establish the gates for analysis (FIG. 6A) and as a positive control for CD41+ staining. As expected, the majority (>85%) of cord blood platelets expressed CD41 (FIG. 6A). Platelets derived from primary MKs cultures that over-expressed the wild-type Livin or Livin$_{RING}$ produced more platelets as compared to empty vector control ($4.3\pm1$ fold, $p=0.02$ and $3\pm0.5$ fold, $p=0.03$, respectively) (FIG. 6B and FIG. 6C). However, only platelets produced by the over-expressing wild-type Livin demonstrated activity in response to arachidonic acid (AA) presence by up regulation of CD62P while the platelets produced in the over-expressing mutant Livin$_{RING}$ showed no activation and thus were not functional (FIG. 6D).

Knock-Down of Livin Reduces Megakaryocytic Differentiation and Function of Human CD34+ Cells siRNA was used to knock down the expression of Livin in human CD34+ cells using a construct containing Livin siRNA (pSUPER-Livin-2) which was previously characterized as a specific and efficient inhibitor of Livin expression[35].

The percent of multi-nucleated MKs ($\geq4$ nuclei) was significantly reduced in the MK cells infected with pSUPER-Livin-2 as compared to control cell cultures ($p=0.033$) (FIG. 7D).

Platelets functionality in response to ADP was similar in the primary MK progenitors as compared to MK cells infected with pSUPER-Livin-2. However, platelets produced from primary MKs progenitors cells that were down-regulated for Livin demonstrated reduced activity in response to AA presence by down regulation of CD62P, and thus seem to be less functional (FIG. 7E).

Taken together, the above results show that over expression of wild-type Livin in CD34+ cells treated with SCF and TPO was accompanied by changes in cell morphology, polyploidization, acquisition of specific MK markers (CD41), and robust expression of both Livin and tLivin in the terminal stage of differentiation. Upon differentiation the above mentioned cells formed pro-platelets and produced functional PLPs capable of aggregation and thus function as normal platelets. Down regulation of Livin decreases significantly MK differentiation and platelets functionality. The pro-apoptotic effect of tLivin did not seem to affect the extent of platelets production, but affected their functionality.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Other References are Cited in the Application

1. Gordge M P. Megakaryocyte apoptosis: sorting out the signals. *Br J Pharmacol*. 2005; 145(3):271-273.
2. Ravid K, Lu J, Zimmet J M, Jones M R. Roads to polyploidy: The megakaryocyte example. *J Cell Physiol*. 2002; 190(1):7-20.
3. Italiano J E, Lecine P, Shivdasani R A, Hartwig J H. Blood platelets are assembled principally at the ends of proplatelet processes produced by differentiated megakaryocytes. *J Cell Biol*. 1999; 147(6): 1299-1312.
4. Handagama P J, Feldman B F, Jain N C, Farver T B, Kono C S. In vitro platelet release by rat megakaryocytes effect of metabolic inhibitors and cytoskeletal disrupting agents. *Am J Vet Res*. 1987; 48(7): 1142-1146.
5. Deutsch V R, Tomer A. Megakaryocyte development and platelet production. *British Journal of Haematology*. 2006; 134(5):453. 466-6. Kile B T. The role of the intrinsic apoptosis pathway in platelet life and death. *J Thromb Haemost*. 2009; 7:214-217.
7. Mason K D, Carpinelli M R, Fletcher J I, et al. Programmed anuclear cell death delimits platelet life span. *Cell*. 2007; 128(6):1173.1186-8. Zhang H, Nimmer P M, Tahir S K, et al. Bcl-2 family proteins are essential for platelet survival. *Cell Death and Differentiation*. 2007; 14(5):943-951.
9. Clarke M C H, Savill J, Jones D B, Noble B S, Brown S B. Compartmentalized megakaryocyte death generates functional platelets committed to caspase-independent death. *J Cell Biol*. 2003; 160(4):577-587.
10. de Botton S, Sabri S, Daugas E, et al. Platelet formation is the consequence of caspase activation within megakaryocytes. *Blood*. 2002; 100(4):1310-1317.
11. Leytin V. Apoptosis in the anucleate platelet. *Blood Reviews*. 2012; 26(2):51-63.
12. Kaluzhny Y, Yu G G, Sun S S, et al. BclxL overexpression in megakaryocytes leads to impaired platelet fragmentation. *Blood*. 2002; 100(5):1670-1678.
13. Ogilvy S, Metcalf D, Print C G, Bath M L, Harris A W, Adams J M. Constitutive Bcl-2 expression throughout the hematopoietic compartment affects multiple lineages and enhances progenitor cell survival. *Proceedings of the National Academy of Sciences of the United States of America*. 1999; 96(26):14943-14948.
14. Bouillet P, Metcalf D, Huang D C S, et al. Proapoptotic Bcl-2 relative bim required for certain apoptotic responses, leukocyte homeostasis, and to preclude autoimmunity. *Science*. 1999; 286(5445):1735-1738.
15. Sanz C, Benet L, Richard C, et al. Antiapoptotic protein Bcl-x(L) is up-regulated during megakaryocytic differentiation of CD34(+) progenitors but is absent from senescent megakaryocytes. *Exp Hematol*. 2001; 29(6):728-735.
16. Kozuma Y, Kojima H, Yuki S, Suzuki H, Nagasawa T. Continuous expression of Bcl-xL protein during megakaryopoiesis is post-translationally regulated by thrombopoietin-mediated Akt activation, which prevents the cleavage of Bcl-xL. *J Thromb Haemost*. 2007; 5(6): 1274-1282.
17. Josefsson E C, James C, Henley K J, et al. Megakaryocytes possess a functional intrinsic apoptosis pathway that must be restrained to survive and produce platelets. *Journal of Experimental Medicine*. 2011; 208(10):2017-2031.
18. Morison I M, Cramer Borde E M, Cheesman E J, et al. A mutation of human cytochrome c enhances the intrinsic apoptotic pathway but causes only thrombocytopenia. *Nature Genetics*. 2008; 40(4):387-389.
19. White M J, Schoenwaelder S M, Josefsson E C, et al. Caspase-9 mediates the apoptotic death of megakaryocytes and platelets, but is dispensable for their generation and function. *Blood*. 2012; 119(18):4283-4290.
20. Winkler J, Rand M L, Schmugge M, Speer O. Omi/HtrA2 and XIAP are components of platelet apoptosis signalling. *Thrombosis and haemostasis*. 2013; 109(3): 532-539.
21. Du C Y, Fang M, Li Y C, Li L, Wang X D. Smac, a mitochondrial protein that promotes cytochrome c-dependent caspase activation by eliminating IAP inhibition. *Cell*. 2000; 102(1):33-42.
22. Verhagen A M, Ekert P G, Pakusch M, et al. Identification of DIABLO, a mammalian protein that promotes apoptosis by binding to and antagonizing IAP proteins. *Cell*. 2000; 102(1):43-53.
23. Suzuki Y, Imai Y, Nakayama H, Takahashi K, Takio K, Takahashi R. A serine protease, HtrA2, is released from the mitochondria and interacts with XIAP, inducing cell death. *Molecular Cell*. 2001; 8(3):613-621.
24. Hegde R, Srinivasula S M, Zhang Z J, et al. Identification of Omi/HtrA-2 as a mitochondrial apoptotic serine protease that disrupts inhibitor of apoptosis protein-caspase interaction. *Journal of Biological Chemistry*. 2002; 277 (1):432-438.
25. Salvesen G S, Duckett C S. IAP proteins: blocking the road to death's door. *Nat Rev Mol Cell Biol*. 2002; 3(6):401-410.
26. Chai J, Shiozaki E, Srinivasula S M, et al. Structural basis of caspase-7 inhibition by XIAP. *Cell*. 2000; 104 (5):769-780.

27. Huang Y, Park Y C, Rich R L, Segal D, Myszka D G, Wu H. Structural basis of caspase inhibition by XIAP: Differential roles of the linker versus the BIR domain. *Cell.* 2000; 104(5):781-790.
28. Nachmias B, Ashhab Y, Ben-Yehuda D. The inhibitor of apoptosis protein family (IAPs): an emerging therapeutic target in cancer. *Semin Cancer Biol.* 2004; 14(4):231-243.
29. Ashhab Y, Alian A, Polliack A, Panet A, Ben Yehuda D. Two splicing variants of a new inhibitor of apoptosis gene with different biological properties and tissue distribution pattern. *FEBS Lett.* 2001; 495(1-2):56-60.
30. Vucic D, Stennicke H R, Pisabarro M T, Salvesen G S, Dixit V M. ML-IAP, a novel inhibitor of apoptosis that is preferentially expressed in human melanomas. *Curr Biol.* 2000; 10(21):1359-1366.
31. Kasof G M, Gomes B C. Livin, a novel inhibitor of apoptosis protein family member. *J Biol Chem.* 2001; 276(5):3238-3246.
32. Nachmias B, Ashhab Y, Bucholtz V, et al. Caspase-mediated cleavage converts Livin from an antiapoptotic to a proapoptotic factor: implications for drug-resistant melanoma. *Cancer Res.* 2003; 63(19):6340-6349.
33. Abd-Elrahman I, Hershko K, Neuman T, Nachmias B, Perlman R, Ben-Yehuda D. The inhibitor of apoptosis protein Livin (ML-IAP) plays a dual role in tumorigenicity. Cancer Research. 2009; 69(13):5475-5480.
34. Nachmias B, Lazar I, Elmalech M, et al. Subcellular localization determines the delicate balance between the anti- and pro-apoptotic activity of Livin. *Apoptosis.* 2007.
35. Crnkovic-Mertens I, Hoppe-Seyler F, Butz K. Induction of apoptosis in tumor cells by siRNA-mediated silencing of the livin/ML-IAP/KIAP gene. Oncogene. 2003; 22(51):8330-8336.
36. Schmollinger J C, Vonderheide R H, Hoar K M, et al. Melanoma inhibitor of apoptosis protein (ML-IAP) is a target for immune-mediated tumor destruction. *Proc Natl Acad Sci USA.* 2003; 100(6):3398-3403.
37. Cheng T, Wang Y S, Dai W. Transcription factor EGR-1 is involved in phorbol 12-myristate 13-acetate-induced megakaryocytic differentiation of K562 cells. *J Biol Chem.* 1994; 269(49):30848-30853.
38. Seigneurin D, Champelovier P, Mouchiroud G, et al. Human chronic myeloid leukemic cell line with positive Philadelphia chromosome exhibits megakaryocytic and erythroid charcteristics. *Exp Hematol.* 1987; 15(8):822-832.
39. Champelovier P, Valiron O, Michele J, Dominique L, Scigncurin D. Selection and charachterization of an erythroeosonophilic subclone (LAMA-88) from the multipotential cell line LAMA-84. *Leuk Res.* 1994; 18(12):903-918.
40. Deveraux Q L, Leo E, Stennicke H R, Welsh K, Salvesen G S, Reed J C. Cleavage of human inhibitor of apoptosis protein XIAP results in fragments with distinct specificities for caspases. *EMBO J.* 1999; 18(19):5242-5251.
41. Pick M, Perry C, Lapidot T, et al. Stress-induced cholinergic signaling promotes inflammation-associated thrombopoiesis. *Blood.* 2006; 107(8):3397-3406.
42. Molla A, Berthier R, Chapel A, Schweitzer A, Andrieux A. Beta-1 integrins mediate adherent phenotype of human erythroblastic cell lines after phorbol 12-myristate 13-acetate induction. *Biochem J.* 1995; 309:491-497.
43. Gurbuxani S, Xu Y F, Keerthivasan G, Wickrema A, Crispino J D. Differential requirements for survivin in hematopoietic cell development. *Proc Natl Acad Sci USA.* 2005; 102(32): 11480-11485.
44. Cailleteau C, Liagre B, Beneytout J L. A proteomic approach to the identification of molecular targets in subsequent apoptosis of HEL cells after diosgenin-induced megakaryocytic differentiation. *J Cell Biochem.* 2009; 107(4):785-796.
45. Lordier L, Jalil A, Aurade F, et al. Megakaryocyte endomitosis is a failure of late cytokinesis related to defects in the contractile ring and Rho/Rock signaling. *Blood.* 2008; 112(8):3164-3174.
46. Wen Q, Leung C, Huang Z, et al. Survivin is not required for the endomitotic cell cycle of megakaryocytes. *Blood.* 2009; 114(1):153-156.
47. Plenchette S, Cathelin S, Rebe C, et al. Translocation of the inhibitor of apoptosis protein c-IAPI from the nucleus to the Golgi in hematopoietic cells undergoing differentiation: a nuclear export signal-mediated event. *Blood.* 2004; 104(7):2035-2043.
48. Pick M, Perry C, Lapidot T, et al. Stress-induced cholinergic signaling promotes inflammation-associated thrombopoiesis. *Blood.* 2006; 107(8):3397-3.406
49. Kanamaru S, Kawano Y, Watanabe T, et al. Low numbers of megakaryocyte progenitors in grafts of cord blood cells may result in delayed platelet recovery after cord blood cell transplant. *Stem Cells.* 2000; 18(3):190-195.

What is claimed is:

1. An isolated population of cells comprising stem cells with a differentiation potential towards platelets or hematopoietic progenitor cells derived therefrom, wherein said stem cells are selected from the group consisting of embryonic stem cells (ESCs), induced pluripotent stem cells (iPS) and hematopoietic stem cells, wherein said stem or progenitor cells comprise a nucleic acid construct comprising a polynucleotide encoding Livin, wherein said Livin comprises:

(i) an anti-apoptotic Livin having an amino acid sequence as set forth in SEQ ID NO: 2 or SEQ ID NO: 6; or
(ii) a pro-apoptotic tLivin having an amino acid sequence as set forth in SEQ ID NO: 4 or SEQ ID NO: 8.

2. The isolated population of cells of claim 1, wherein said hematopoietic progenitor cells are selected from the group consisting of myeloid precursor cells and megakaryocytes.

3. The isolated population of cells of claim 1, having an increased ploidy as compared to stem cells with a differentiation potential towards platelets or hematopoietic progenitor cells derived therefrom not comprising said nucleic acid construct, as assayed by flow cytometry.

4. The isolated population of cells of claim 1, having an increased number of nuclei per cell as compared to stem cells with a differentiation potential towards platelets or hematopoietic progenitor cells derived therefrom not comprising said nucleic acid construct, as assayed by May Grumwald/Giemsa staining.

5. The isolated population of cells of claim 1, comprising a platelet production stimulating factor.

6. The isolated population of cells of claim 5, wherein said platelet production stimulating factor is selected from the group consisting of thrombopoietin (TPO), TPO agonist, stem cell factor (SCF) and Phorbol myristate acetate (PMA).

* * * * *